United States Patent
Yamamoto et al.

(10) Patent No.: US 9,766,227 B2
(45) Date of Patent: Sep. 19, 2017

(54) SCREENING METHOD FOR SUBSTANCE HAVING HEMOCYTE MATURATION ACCELERATION ACTION

(75) Inventors: Tetsuro Yamamoto, Kumamoto (JP); Hiroshi Nishiura, Kumamoto (JP); Hideki Saito, Tokyo (JP)

(73) Assignee: Bloom Technology Co., Ltd., Tokyo (JP)

(*) Notice: Subject to any disclaimer, the term of this patent is extended or adjusted under 35 U.S.C. 154(b) by 749 days.

(21) Appl. No.: 13/697,811

(22) PCT Filed: May 13, 2011

(86) PCT No.: PCT/JP2011/061057
§ 371 (c)(1),
(2), (4) Date: Jun. 26, 2013

(87) PCT Pub. No.: WO2011/142457
PCT Pub. Date: Nov. 17, 2011

(65) Prior Publication Data
US 2013/0310544 A1 Nov. 21, 2013

(30) Foreign Application Priority Data
May 14, 2010 (JP) ................................ 2010-112556

(51) Int. Cl.
| C12N 5/00 | (2006.01) |
| G01N 33/50 | (2006.01) |
| G01N 33/80 | (2006.01) |
| C12N 5/078 | (2010.01) |

(52) U.S. Cl.
CPC ....... *G01N 33/5044* (2013.01); *C12N 5/0641* (2013.01); *G01N 33/5094* (2013.01); *G01N 33/80* (2013.01); *G01N 2500/10* (2013.01)

(58) Field of Classification Search
None
See application file for complete search history.

(56) References Cited

FOREIGN PATENT DOCUMENTS

JP 2006-94827 A 4/2006

OTHER PUBLICATIONS

Pali et al., ( Blood, 2010, v.116, Abstract 2244.*
Hansson et al ., Stem Cells, 2007, V.25, pp. 1507-1510.*
De St. Groth et al. "T cell activation: in vivo veritas" Immunology and Cell Biology 2004, 82: 260-268.*
Berthebaud, M., et al., "RGS16 is a negative regulator of SDF-1—CXCR4 signaling in megakaryocytes," *Blood* 106:2962-2968, The American Society of Hematology, United States (2005).
Draptchinskaia, N., et al., "The gene encoding ribosomal protein S19 is mutated in Diamond-Blackfan anaemia," *Nature Genetics* 21:169-175, Nature Publishing Group, England (1999).
Flygare, J., et al., "Human RPS19, the gene nutated in Diamond-Blackfan anemia, encodes a ribosomal protein required for the maturation of 40S ribonsomal subunits," *Blood* 109:980-986, The American Society of Hematology, United States (2007).
Gazda, H.T., and Sieff, C.A., "Recent insights into the pathogenesis of Diamond-Blackfan anaemia," *British Journal of Haematology* 135:149-157, Blackwell Publishing Ltd, England (2006).
Horino, K., et al., "A Monocyte Chemotactic Factor, S19 Ribosomal Protein Dimer, in Phagocytic Clearance of Apoptotic Cells," *Laboratory Investigation* 78:603-617, The United States and Canadian Academy of Pathology, Inc. United States (1998).
Idol, R.A., et al., "Cells depleted for RPS19, a protein associated with Diamond Blackfan Anemia, show defects in 18S ribosomal RNA synthesis and small robosomal subunit production," *Blood Cells, Molecules, and Diseases* 39:35-43, Elsevier Inc., United States (2007).
Kaushansky, K., "Historical review: megakaryopoiesis and thrombopoiesis," *Blood* 111:981-986, The American Society of Hematology, United Sates (2008).
Liu, J.M., and Ellis, S.R., "Ribosomes and marrow failure: coincidental association or molecular paradigm?," *Blood* 107:4583-4588, The American Society of Hematology, United Stated (2006).
Miyake, K., et al., "Development of Cellular Models for Ribosomal Protein S19 (RPS19)-Deficient Diamond-Blackfan Anemia Using Inducible Expression of siRNA against RPS19," *Molecular Therapy* 11:627-637, The American Society of Gene Therapy, United Stated (2005).
Nagata, Y., et al., "A novel regulator of G-protein signaling bearing GAP activity for Gαi and Gαq in megakaryocytes," *Blood* 97:3051-3060, The American Society of Hematology, United Stated (2001).
Nishiura, H., et al., "Monocyte Chemotactic Factor in Rheumatoid Arthritis Synovial Tissue," *The Journal of Biological Chemistry* 271:878-882, The American Society for Biochemistry and Molecular Biology, Inc., United States (1996).

(Continued)

*Primary Examiner* — Michail Belyavskyi
(74) *Attorney, Agent, or Firm* — Sterne, Kessler, Goldstein & Fox P.L.L.C.

(57) ABSTRACT

An objective is to provide screening methods for substances having an activity of promoting maturation into hemocytes. It was revealed that in the maturation process of erythrocytes and platelets, RP S19 multimers are released to the outside of the cell and act on the C5a receptors of erythroblasts and megakaryocytes, thereby causing maturation of erythroblasts and megakaryocytes to erythrocytes and platelets. Based on such findings, the present invention provides methods of screening for substances having an activity of promoting maturation into hemocytes by targeting the RP S19 multimers and C5a receptors. The screening methods of the present invention can detect hemocyte maturation using an increase of the R4 RGS family as an indicator. Furthermore, the present invention provides agents for promoting hemocyte maturation, which comprise RP S19 multimers and a substance having an activity of promoting maturation into hemocytes as useful components. The present invention also provides methods for producing erythrocytes and platelets, which include the step of contacting RP S19 multimers and a substance having an activity of promoting maturation into hemocytes with erythroblasts or megakaryocytes.

8 Claims, 13 Drawing Sheets

(56) References Cited

OTHER PUBLICATIONS

Nishiura, H., et al., "Pro- and anti-apoptotic dual functions of the C5a receptor: involvement of regulator of G protein signaling 3 and extracellular signal-regulated kinase," *Laboratory Investigation* 89:676-694, USCAP, Inc, United States (2009).

Nishiura, H., et al., "S19 Ribosomal Protein Cross-Linked Dimer Causes Monocyte-Predominant Infiltration by Means of Molecular Mimicry to Complement C5a," *Laboratory Investigation* 78:1615-1623, The United States and Canadian Academy of Pathology, Inc., United States (1998).

Nishiura, H., et al., "S19 Ribosomal Protein Dimer Augments Metal-Induced Apoptosis in a Mouse Fibroblastic Cell Line by Ligation of the C5a Receptor," *Journal of Cellular Biochemistry* 94:540-553, Wiley-Liss, Inc., United States (2005).

Patel, S.R., et al., "The biogenesis of platelets from megakaryocyte proplatelets,"*The Journal of Clinical Investigation* 115:3348-3354, American Society for Clinical Investigation, United States (2005).

Scheschonka, A., et al., "RGS3 Is a GTPase-Activating Protein for $G_{i\alpha}$ and $G_{q\alpha}$ and a Potent Inhibitor of Signaling by GTPase-Deficient Forms of Gqα and $G_{11\alpha}$," *Molecular Pharmacology* 58:719-728, The American Society for Pharmacology and Experimental Therapeutics, United States (2000).

Willig, T.-N., et al., "Mutations in Ribosomal Protein S19 Gene and Diamond Blackfan Anemia: Wide Variations in Phenotypic Expression," *Blood* 94:4294-4306, The American Society of Hematology, United States (1999).

Yowe, D., et al., "RGS18 is a myeloerythroid lineage-specific regulator of G-protein-signalling molecule highly expressed in megakaryocytes," *Biochem. J.* 359:109-118, Biochemical Society, Great Britain (2001).

International Search Report for International Application No. PCT/JP2011/061057, Japanese Patent Office, Japan, mailed on Aug. 2, 2011.

Ebert, B.L. et al., "An RNA interference model of RPS19 deficiency in Diamond-Blackfan anemia recapitulates defective hematopoiesis and rescue by dexamethasone: identification of dexamethasone-responsive genes by microarray,"*Blood* 105:4620-4626, American Society of Hematology (2005).

Supplementary European Search Report for European Patent Appl. No. Ep 11 78 0712, completed Aug. 28, 2013, The Hague, The Netherlands.

Shibuya, Y., et al., "Identification of Receptor-Binding Sites of Monocyte Chemotactic S19 Ribosomal Protein Dimer," *Am. J of Pathology* 159 (6):2293-2301, American Society for Investigative Pathology, United States (2001).

Chou, C.C., and Hsu, C.Y., "Involvement of PKC in TPA-potentiated apoptosis induction during heroin-mediated erythroid differentiation in K562 cells," *Naunyn-Schmiedeberg's Arch Pharmacol* 379:1-9, Springer-Verlag, Germany (2009).

Huo, X-F, et al., "Differential expression changes in K562 cells during the hemin-induced erythroid differentiation and the phorbol myristate acetate (PMA)-induced megakaryocytic differentiation," *Molecular and Cellular Biochemistry* 292:155-167, Springer, Germany (2006).

Iwasaki, K., et al., "Heroin-Mediated Regulation of an Antioxidant-Responsive Element of the Human Ferritin H Gene and Role of Ref-1 during Erythroid Differentiation of K562 Cells," *Molecular and Cellular Biology* 26(7):2845-2856, American Society for Microbiology, United States (2006).

Kucukkaya, B., et al., "Role of G proteins and ERK activation in hemin-induced erythroid differentiation of K562 cells," *Life Sciences* 78:1217-1224, Elsevier Inc., United States (2006).

Leppa, S., et al., "Overexpression of FISF2-β Inhibits Hemin-induced Heat Shock Gene Expression and Erythroid Differentiation in K562 Cells," *The Journal of Biological Chemistry* 272(24):15293-15298, The American Society for Biochemistry and Molecular Biology, Inc., United States (1997).

Li, X-F., et al., "Hemin-induced Erythroid Differentiation Changes the Sensitivity of K562 Cells to Tumor Necrosis Factor-α," *Exp Hematol* 17:1059-1062, International Society for Experimental Hematology, United States (1989).

Nakajima, O., et al., "Enhancement by retinoid of hemin-induced differentiation of human leukemia K562 cell line," *FEBS* 330(1):81-84, Elsevier Science B.V., Netherlands (1993).

Nakajima, O., et al., "Hemin-Induced Erythroid Differentiation of Human Myeloleukemia K562 Cell Line and its Modification by Bioresponse Modifiers," *Cellular and Molecular Biology* 43(1):115-134, Noisy-le-Grand, France (1997).

Okabe-Kado, J., et al., "Effects of Inducers of Erythroid Differentiation of Human Leukemia K562 Cells on Vincristine-Resistant K562/VCR Cells," *Leukemia Research* 7(4):481-485, Pergamon Press Ltd., England (1983).

Pinho, F.O., et al., "Reduction of AHSP synthesis in hemin-induced K562 cells and EPO-induced CD34+ cells leads to α-globin precipitation, impairment of normal hemoglobin production, and increased cell death," *Experimental Hematology* 36:265272, Elsevier Inc., United States (2008).

Schnekenburger, M., et al., "Increased glutathione S-transferase P1-1 expression by mRNA stabilization in hemin-induced differentiation of K562 cells," *Biochemical Pharmacology* 68:1269-1277, Elsevier Inc., United States (2004).

Shiraishi, M., et al., "A high concentration of triiodothyronine attenuates the stimulatory effect of hemin-induced erythroid differentiation of human erythroleukemia K562 cells," *Endocrine Journal* 62(5):431-440, The Japan Endocrine Society, Japan (2015).

Song, M.S., et al., "Voltage-Gated $K^+$ Channel, Kv3.3 Is Involved in Hemin-Induced K562 Differentiation," *PLOS One* 11(2):e0148633, Open Access, 19 pages (2016).

Rutherford, T.R., et al., "K562 human leukaemic cells synthesise embryonic haemoglobin in response to haemin," *Nature* 280:164-165, Nature Publishing Group, England (1979).

Theodorakis, N.G., et al., "Hemin-Induced Transcriptional Activation of the HSP70 Gene during Erythroid Maturation in K562 Cells Is Due to a Heat Shock Factor-Mediated Stress Response," *Molecular and Cellular Biology* 9(8):3166-3173, American Society for Microbiology, United States (1989).

Tomoda, T., et al., "Fluctuation of gene expression for poly(ADP-ribose) synthetase during hemin-induced erythroid differentiation of human leukemia K562 cells and its reversion process," *Biochimica et Biophysica Acta* 1088:359-364, Elsevier Science Publishers B.V., Netherlands (1991).

Fujiwara, T., et al., "Forced FOG1 expression in erythroleukemia cells: Induction of erythroid genes and repression of myelo-lymphoid transcription factor PU.1.," *Biochem Biophys Res Commun* 485(2):380-387, Elsevier Inc., United States (2017) (Abstract only).

Li, Y., et al., "MicroRNA 200a inhibits erythroid differentiation by targeting PDCD4 and THRB," *Br J Haematol* 176(1):50-64, John Wiley & Sons Ltd., United States (2017) (Abstract only).

Li, Y., et al., "miR-218 Inhibits Erythroid Differentiation and Alters Iron Metabolism by Targeting ALAS2 in K562 Cells," *International Journal of Molecular Sciences* 16:28156-28168, MDPI, Switzerland (2015).

Luo, S.-T., et al., "The Promotion of Erythropoiesis via the Regulation of Reactive Oxygen Species by Lactic Acid," *Scientific Reports* 7:38105, 12 pages, Nature Publishing Group, England (2017).

Naarmann-De Vries, I.S., et aL, "Translational control mediated by hnRNP K links NMHC IIA to erythroid enucleation," *Journal of Cell Science* 129:1141-1154, Company of Biologists Ltd., United States (2016).

Shariati, L., et al., "Comparison of different methods for erythroid differentiation in the K562 cell line," *Biotechnol Lett* 38(8):1243-1250, Kluwer Academic Publishers, Netherlands (2016) (Abstract only).

Sun, Z., et al., "miR-150 inhibits terminal erythroid proliferation and differentiation," *Oncotarget* 6(40):43033-43047, Impact Journals, United States (2015).

Wani, S., et al., "Human SCP4 is a chromatin-associated CTD phosphatase and exhibits the dynamic translocation during erythroid differentiation," *J Biochem* 160(2):111-120, Oxford University Press, England (2016) (Abstract only).

(56) References Cited

OTHER PUBLICATIONS

Wu, J., et al., "Protein phosphatase 2A regulatory subunit B56β modulates erythroid differentiation," *Biochemical and Biophysical Research Communications* 478(3):11791184, Elsevier, United States (2016) (Abstract only).

* cited by examiner

SCREENING METHOD FOR SUBSTANCE HAVING HEMOCYTE MATURATION ACCELERATION ACTION

TECHNICAL FIELD

The present invention relates to methods of screening for substances having an activity of promoting maturation into hemocytes. Furthermore, the present invention relates to agents that promote maturation into hemocytes, which comprise as an active ingredient S19 ribosomal protein (RP S19) multimers and/or a substance having an activity of promoting maturation into hemocytes. Furthermore, the present invention relates to methods for producing hemocytes using RP S19 multimers and/or a substance having an activity of promoting maturation into hemocytes.

BACKGROUND ART

Mitotic proliferation of precursor cells, and differentiation and maturation of daughter cells produced by them are necessary for hematopoiesis. Regarding the former, stem cells in several differentiation stages, microenvironments called niches, and growth factors for the respective stem cells are clearly important. Erythropoietin and thrombopoietin are the most important growth factors for hematopoiesis of erythrocytes and hematopoiesis of megakaryocytes and platelets, respectively. Meanwhile, a lot is still unclear regarding differentiation and maturation of the latter. It is fundamental to sort which of the estimated 23,000 human genes to use as a set and which ones not to use for regular cell differentiation and maturation.

In most cells that constitute a living organism, intracellular organelles including the nucleus are maintained even after maturation. On the other hand, some hemocytes such as erythrocytes and platelets lack organelles such as the nucleus.

Thus, differentiation and maturation in adult-type (non-fetal-type) erythropoiesis discard most organelles such as the nucleus and mitochondria, and are completely different processes from regular cell differentiation and maturation. The maturation process in thrombopoiesis is also a dramatic process, and involves enucleation of the nucleus along with release of the whole cytoplasm containing megakaryocyte organelles in the form of several thousand vesicles enveloped by the cell membrane. A hypothesis was proposed at the end of the 1990's that an apoptosis mechanism is actively used in such enucleation, disposal of organelles, and reconstitution of cells to corpuscles, and its verification has become an important research subject. Furthermore, in erythroid differentiation and maturation in the bone marrow, structures called the hematopoietic islands are formed. These are assemblies of erythroblasts formed around macrophages at the center, and thus it is expected that bone marrow macrophages are involved in erythroid differentiation and maturation. Based on the fact that many unprocessed phagocytosed nuclei were left inside the cytoplasm of bone marrow macrophages when DNAase II gene knockout mice prepared in the early 2000's unexpectedly showed embryonic death due to anemia, macrophages were found to be involved in the phagocytosis of enucleation products and such derived from erythroblasts.

On the other hand, when investigating the mechanism of removal of apoptotic cells, the present inventors discovered that when cells receive an apoptosis-inducing stimulus, the S19 ribosomal protein (RP S19), which is a constituent molecule of the ribosome, i.e., the protein synthesis (translation) machinery, becomes cross-linked multimers (dimers or larger oligomers) by the enzymatic activity of cytoplasmic transglutaminase and is released to the outside of the cells [Non-Patent Document 1]. Furthermore, the present inventors elucidated that RP S19 acquires the ability through multimerization to bind to the C5a receptor(s) [Non-Patent Document 2]. C5a receptors were identified as receptors of complement C5a which is a leukocyte chemotactic factor. The present inventors discovered that cells which have received an apoptosis-inducing stimulus start to produce the C5a receptor(s), and that released RP S19 multimers promote apoptosis via the C5a receptor(s) [Non-Patent Document 3]. On the other hand, it was also elucidated that RP S19 multimers recruit monocytes and macrophages by binding to the C5a receptor(s), and make them phagocytose apoptotic cells through local infiltration [Non-Patent Document 4]. That is, RP S19 multimers are thought to achieve smooth phagocytosis of apoptotic cells by synchronizing the execution of apoptosis and recruitment of phagocytic cells.

Regarding hematopoiesis, growth factors for the respective lineages of precursor cells have been identified. For example, recombinants of growth factors such as erythropoictin and thrombopoietin have become available for use, and revolutionary advances are seen in treatments for anemia and thrombocytopenia. However, treatment-resistant hematopoietic failures, which do not respond to growth factors, still remain. Hematopoietic failures can be classified into congenital and acquired, but in either case, establishment of novel therapeutic methods is needed for diseases that are not therapeutically ineffective by growth factors. It is speculated that many hematopoietic failures that do not respond to growth factors are those with abnormalities in the maturation process, i.e., final differentiation of precursor cells such as erythroblasts and megakaryocytes into hemocytes such as erythrocytes and platelets.

It has been reported that RP S19 gene abnormality (heterozygous abnormality) is the cause for 25% of the cases in children's congenital anemia (Diamond-Blackfan anemia) [Non-Patent Documents 5 and 6]. On the other hand, RP S19 is a constituent molecule of ribosome, and this molecule has been reported to be essential for ribosome production (ribosome biogenesis) [Non-Patent Documents 7 and 8]. Previously, it was speculated that involvement of RP S19 abnormality in the development of anemia is mediated by insufficient protein synthesis (translation) ability in erythroblastic cells due to a decrease in the number of ribosomes caused by inadequate ribosome biogenesis. However, direct evidence related to this has not been found, and naturally there are also opposing views of this speculation [Non-Patent Document 9]. Thus, the reason why heterozygous abnormality of the RP S19 gene causes congenital anemia is still unclear.

In the past, factors regulating the final differentiation of the megakaryocytic lineage, or specifically, platelet biogenesis have not been elucidated [Non-Patent Documents 10 and 11].

PRIOR ART DOCUMENTS

Non-Patent Documents

[Non-Patent Document 1] Monocyte chemotactic factor in rheumatoid arthritis synovial tissue. Probably a cross-linked derivative of S19 ribosomal protein., Nishiura H, Shibuya Y, Matsubara S, Tanase S, Kambara T, Yamamoto T., J Biol Chem. 1996 Jan. 12; 271(2):878-82.

[Non-Patent Document 2] S19 ribosomal protein cross-linked dimer causes monocyte-predominant infiltration by means of molecular mimicry to complement C5a., Nishiura H, Shibuya Y, Yamamoto T., Lab Invest. 1998 December; 78(12):1615-23.

[Non-Patent Document 3] Nishiura H, Tanase S, Shibuya Y, Futa N, Sakamoto T, Higginbottom A, Monk P, Zwirner J, Yamamoto T., J Cell Biochem. 2005 94, 540-553.

[Non-Patent Document 4] A monocyte chemotactic factor, S19 ribosomal protein dimer, in phagocytic clearance of apoptotic cells., Horino K, Nishiura H, Ohsako T, Shibuya Y, Hiraoka T, Kitamura N, Yamamoto T. Lab Invest. 1998 May; 78(5):603-17.

[Non-Patent Document 5] Draptchinskaia N et al. The gene encoding ribosomal protein S19 is mutated in Diamond-Blackfan anemia. Nature genetics 1999 21, 169-174.

[Non-Patent Document 6] Willig T N et al. Mutations in ribosomal protein S19 gene and Diamond-Blackfan anemia: wide variations in phenotypic expression. Blood 1999 94, 4294-4306.

[Non-Patent Document 7] Flygare J et al. Human RPS19, the gene mutated in Diamond-Blackfan anemia, encodes a ribosomal protein required for the maturation of 40S ribosomal subunits. Blood 2007 109, 980-986.

[Non-Patent Document 8] Idol R A et al. Cells depleted for RPS19, a protein associated with Diamond Blackfan anemia, show defects in 18S ribosomal RNA synthesis and small ribosomal subunit production. Blood Cells Mol Dis 2007 39, 35-43.

[Non-Patent Document 9] Liu J M, Ellis S R; Ribosomes and marrow failure: coincidental association or molecular paradigm? Blood 2006 107, 4583-4588.

[Non-Patent Document 10] Patel S R, Hartwig J H, Italiano J E Jr.: The biogenesis of platelets from megakaryocyte proplatelets. J Clin Invest 2005 115, 3348-3354.

[Non-Patent Document 11] Kaushansky K: Historical review: megakaryopoiesis and thrombopoiesis. Blood. 2008 111, 981-986

SUMMARY OF THE INVENTION

Problems to be Solved by the Invention

As previously mentioned, it has become possible to treat anemia and thrombocytopenia by using growth factors such as erythropoietin and thrombopoietin. However, there are more than a few hematopoietic failure patients whose symptoms do not improve with these growth factors. Patients who do not respond to growth factor treatment may have abnormalities in the maturation process into hemocytes. Therefore, if one can elucidate the mechanism that prompts maturation of hemocyte precursor cells into hemocytes, and provide a method for finding compounds that promote maturation, it is possible to attain novel therapeutic techniques for hematopoietic failure.

An objective of the present invention is to provide methods of screening for substances having an activity to promote maturation into hemocytes (particularly erythrocytes and platelets). Furthermore, an objective of the present invention is to provide agents for promoting maturation into hemocytes, which include as active ingredients an RP S19 multimer and/or a substance having an activity to promote maturation into hemocytes. Another objective of the present invention is to provide methods for producing hemocytes using an RP S19 multimer and/or a substance having an activity of promoting maturation into hemocytes.

Means for Solving the Problems

The present inventors newly found that the mechanism of processing apoptotic cells mediated by RP S19 multimers contributes to enucleation of erythroblasts and processing of the nuclei. During this study, the present inventors also found that in the biogenesis and release of platelets from megakaryocytes, RP S19 multimers produced and released from the megakaryocytes themselves promote this process. Therefore, RP S19 separates from the ribosomes in the maturation process of erythroblasts and megakaryocytes. It is crosslinked and multimerized by intracellular transglutaminase activity, and released to the outside of the cell. By acting on the C5a receptor(s) of erythroblasts and megakaryocytes, it promotes final maturation including enucleation of erythroblasts and proplatelet formation by megakaryocytes. On the other hand, RP S19 multimers were found to be involved in the final maturation into erythrocytes and platelets by acting on the C5a receptor(s) on macrophages, and promote phagocytic processing of enucleation products and such. Furthermore, the present inventors discovered that delta lactoferrin (δLf) and delta annexin A3 (δANXA3) may be involved in apoptosis and the process of maturation of hemocyte precursor cells into hemocytes as described below, and thereby induce expression of the regulator of G-protein signaling 3 (RGS3) gene. Specifically, the C-terminal twelve-amino-acid-residue portion of RP S19 binds to a complex of delta lactoferrin and delta annexin A3. Delta lactoferrin translocates to the nucleus and induces the expression of RGS3 as a transcription factor.

Furthermore, the present inventors discovered that in the process of maturation into hemocytes, not only the expression of RGS3 but also that of other R4 RGS family members is induced.

In congenital anemia (Diamond-Blackfan anemia) which has RP S19 gene abnormality, inhibition of hemocyte maturation due to inadequate ribosome biogenesis was presumed to be the mechanism of development. However, the present inventors discovered that RP S19 is involved in hematopoiesis in a form completely unrelated to ribosome which is the translation machinery; i.e., it provides a non-ribosomal function. Accordingly, the inventors found out that RP S19 which is originally an intracellular protein has a function of promoting maturation of erythroblasts upon release to the outside of the cell, and that this functional abnormality is accountable for the mechanism of anemia development.

The present invention is based on these findings and relates to the following invention:

[1] a method of screening for a substance having an activity of promoting maturation into hemocytes, which comprises the steps of:
(a) contacting a test substance with a hemocyte precursor cell;
(b) detecting an increase in the R4 RGS family in the hemocyte precursor cell; and
(c) selecting a test substance that promotes the increase of the R4 RGS family in the hemocyte precursor cell compared to a control;

[2] the method of [1], wherein the hemocyte precursor cell expresses a C5a receptor(s) and the increase in the R4 RGS family is promoted via the C5a receptor(s);

[3] the method of [2], which is performed in the presence of RP S19;

[4] the method of [2] or [3], which comprises the step of mixing a test substance with an RP S19 monomer prior to step (a), and which uses the mixture of the test substance and RP S19 monomer obtained in this step as the test substance in step (a);

[5] the method of any one of [1] to [4], wherein the hemocyte precursor cell is an erythroblast;

[6] the method of [5], wherein step (b) further comprises a step of detecting an erythrocyte;

[7] the method of [5], wherein step (b) further comprises a step of detecting enucleation of an erythroblast;

[8] the method of [5], wherein step (b) is a step of detecting an increase in the expression of an R4 RGS family gene;

[9] the method of [5], wherein step (b) is a step of detecting an increase in an R4 RGS family protein;

[10] the method of any one of [1] to [9], wherein the R4 RGS family is selected from the group consisting of RGS1, RGS3, RGS16, and RGS18;

[11] the method of any one of [1] to [4], wherein the hemocyte precursor cell is a megakaryocyte;

[12] the method of [11], wherein step (b) further comprises a step of detecting a platelet;

[13] a substance having a hemocyte maturation-promoting activity, which is obtained from the method of any of [1] to [12];

[14] an agent for promoting maturation into hemocytes, which comprises as an active ingredient an RP S19 multimer and/or the substance of [13];

[15] the promoting agent of [14] for inducing an erythrocyte and/or a platelet;

[16] a method for producing an erythrocyte and/or a platelet, which comprises the step of contacting a hemocyte precursor cell with an RP S19 multimer and/or the substance of [13];

[17] the method of [16], wherein the hemocyte precursor cell is an erythroblast and/or a megakaryocyte;

[18] a method for promoting maturation into hemocytes, wherein the method comprises the step of administering an RP S19 multimer and/or the substance of [13] to a subject;

[19] the method of [18] for inducing an erythrocyte and/or a platelet;

[20] use of an RP S19 multimer and/or the substance of [13] in the manufacture of an agent for promoting maturation into hemocytes;

[21] the use of [20] for inducing an erythrocyte and/or a platelet;

[22] an RP S19 multimer and/or the substance of [13] for promoting maturation into hemocytes;

[23] an RP S19 multimer and/or the substance of [22] for inducing an erythrocyte and/or a platelet;

[24] use of an RP S19 multimer and/or the substance of [13] for promoting maturation into hemocytes; and

[25] the use of [24] for inducing an erythrocyte and/or a platelet.

Furthermore, the present invention relates to the following:

[101] a method of screening for a substance having an activity to promote maturation into hemocytes, which comprises the steps of:
(a) contacting a test substance with a hemocyte precursor cell expressing a C5a receptor(s);
(b) detecting maturation of the hemocyte precursor cell mediated by the C5a receptor(s); and
(c) selecting a test substance that promotes maturation of the hemocyte precursor cell compared to a control;

[102] the method of [101], wherein the method is carried out in the presence of RP S19;

[103] the method of [101] or [102], which comprises the step of mixing a test substance with an RP S19 monomer prior to step (a), and which uses the mixture of the test substance and RP S19 monomer obtained in this step as the test substance in step (a);

[104] the method of any one of [101] to [103], wherein the hemocyte precursor cell is an erythroblast;

[105] the method of [104], wherein the step of detecting maturation of the hemocyte precursor cell in step (b) is a step of detecting an erythrocyte;

[106] the method of [104], wherein the step of detecting maturation of the hemocyte precursor cell in step (b) is a step of detecting enucleation of an erythroblast;

[107] the method of [104], wherein the step of detecting maturation of the hemocyte precursor cell in step (b) is a step of detecting an increase in the expression of at least one gene from RGS1, RGS3, RGS16, and RGS18;

[108] the method of [104], wherein the step of detecting maturation of the hemocyte precursor cell in step (b) is a step of detecting an increase in at least one protein from RGS1, RGS3, RGS16, and RGS 8;

[109] the method of any one of [101] to [103], wherein the hemocyte precursor cell is a megakaryocyte;

[110] the method of [109], wherein the step of detecting maturation of the hemocyte precursor cell of step (b) is a step of detecting a platelet;

[111] a substance obtained from the methods of [101] to [110] and has a hemocyte maturation-promoting activity;

[112] an agent for promoting maturation into hemocytes, which comprises an RP S19 multimer and/or the substance of [111] as an active ingredient;

[113] the promoting agent of [112] for inducing an erythrocytes and/or a platelet;

[114] a method for producing an erythrocyte and/or a platelet, which comprises the step of contacting an RP S19 multimer and/or the substance of [111] with a hemocyte precursor cell;

[115] the method of [114], wherein the hemocyte precursor cell is an erythroblast and/or a megakaryocyte;

[116] a method for promoting maturation into hemocytes, which comprises the step of administering to a subject an RP S19 multimer and/or the substance of [111];

[117] the method of [116] for inducing an erythrocyte and/or a platelet;

[118] use of an RP S19 multimer and/or the substance of [111] in the manufacture of an agent for promoting maturation into hemocytes;

[119] use of [118] for inducing an erythrocyte and/or a platelet;

[120] an RP S19 multimer and/or the substance of [111] for promoting maturation into hemocytes;

[121] the RP S19 multimer and/or the substance of [120] for inducing an erythrocyte and/or a platelet;

[122] use of an RP S19 multimer and/or the substance of [111] for promoting maturation into hemocytes; and

[123] use of [122] for inducing an erythrocyte and/or a platelet.

Effects of the Invention

The present invention provides methods of screening for substances having an activity to promote maturation into hemocytes. It is possible to obtain substances having an activity to promote maturation into hemocytes (for example, erythrocytes and platelets) by the screening methods. Substances having an activity to promote maturation into hemocytes are useful as candidate substances for therapeutic agents of treatment-resistant hematopoietic failure and such which do not respond to growth factors for hemocyte precursor cells.

Specifically, the present invention elucidated that binding of an RP S19 multimer to the C5a receptor(s) is involved in hematopoiesis. Therefore, RP S19 multimers are also useful as candidate substances for hemocyte maturation-promoting agents.

BRIEF DESCRIPTION OF THE DRAWINGS

FIG. 8-1 presents diagrams showing a culture method for assisting induction of K562 cell differentiation and differentiation markers. As a result of adding manganese to culture when inducing differentiation of K562 cells with hemin, CD71-positive cells were confirmed on day 3, and the number of days taken for maturation until erythroblast formation was reduced.

FIG. 8-2 presents diagrams showing a culture method for assisting induction of K562 cell differentiation and differentiation markers. As a result of adding manganese to culture, the number of days taken for maturation until erythroblast formation was reduced. Lactoferrin (Lf) and C5a receptor (CD88) were used as the differentiation markers.

FIG. 8-3 presents diagrams showing a culture method for assisting induction of K562 cell differentiation and differentiation markers. As a result of adding manganese to culture, the number of days taken for maturation until erythroblast formation was reduced. FAS ligand (CD178) and C5a receptor (CD88) were used as the differentiation markers.

MODE FOR CARRYING OUT THE INVENTION

Figure 1:
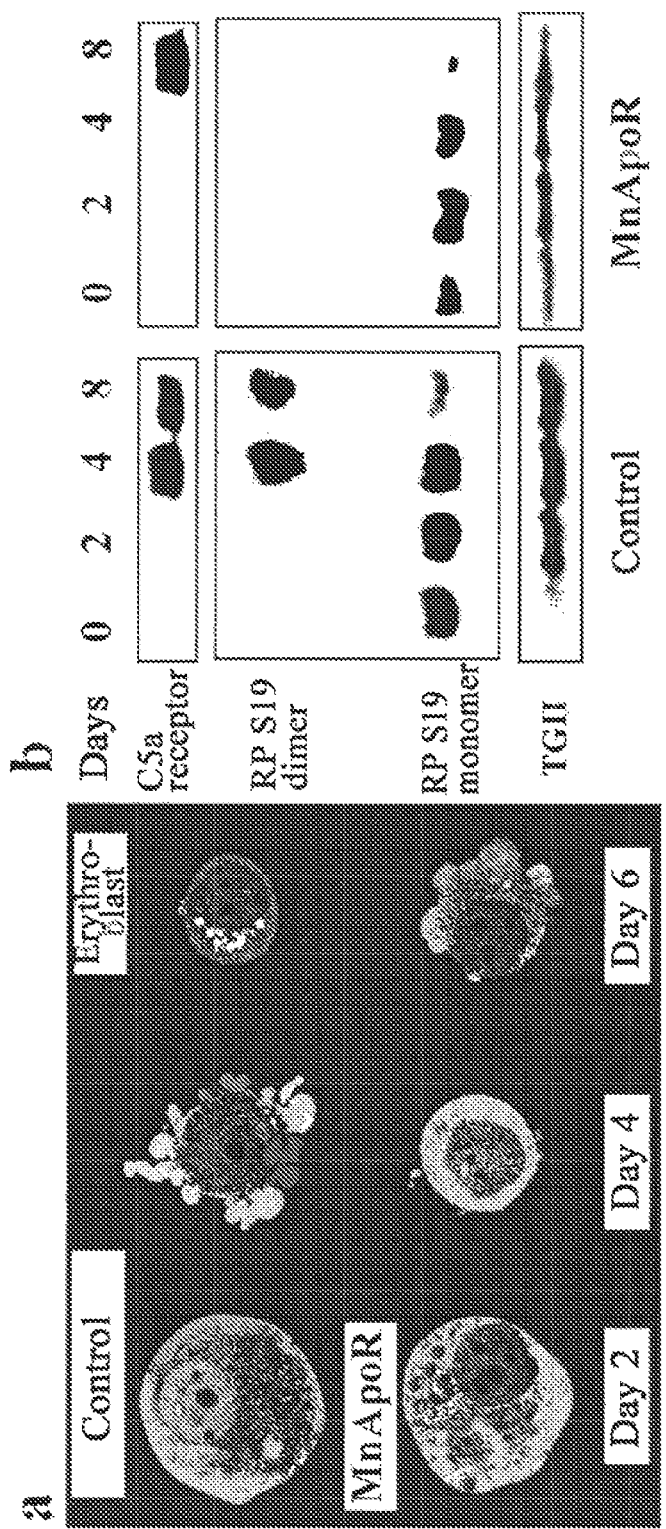
FIG. 1 presents photographs showing effects of the RP S19 multimer/C5a receptor(s) mechanism on hemin-induced erythroblastic differentiation of K562 cells. In mutant K562 cells (MnApoR) which do not undergo apoptosis, formation of RP S19 multimers is inhibited, and maturation of erythrocytes is delayed.

The present inventors discovered that RP S19 and C5a receptor(s) are involved in the process of maturation of erythroblasts and megakaryocytes into erythrocytes and platelets. Specifically, the present inventors discovered that RP S19 multimers released to the outside of the cell act on the C5a receptor(s) of erythroblasts and megakaryocytes to promote final maturation including enucleation of erythroblasts and proplatelet formation by megakaryocytes. Furthermore, the present inventors discovered that RGS3 expression may be induced by involvement of delta lactoferrin (δLf) and delta annexin A3 (δANXA3) in the apoptosis process and maturation of hemocyte precursor cells into hemocytes as described below. Specifically, the twelve-amino-acid-residue portion in the C terminus of RP S19 binds to the complex formed by delta lactoferrin and delta annexin A3. Delta lactoferrin translocates into the nucleus and as a transcription factor induces RGS3 expression.

Furthermore, the present inventors showed that not only the expression of RGS3 but also that of the R4 RGS family is induced in the process of maturation into hemocytes, and may become markers of erythrocyte differentiation.

Based on these findings, the present inventors showed that promoting hemocyte maturation mediated by the C5a receptor(s) is an effective strategy for treating treatment-resistant hematopoietic failures and such which do not respond to growth factors such as erythropoietin and thrombopoietin.

Specifically, the present invention relates to a method of screening for a substance having an activity of promoting maturation into hemocytes, which comprises the steps of:
(a) contacting a test substance with hemocyte precursor cells;
(b) detecting an increase of the R4 RGS family in the hemocyte precursor cells; and
(c) selecting a test substance that promotes the increase of R4 RGS family in the hemocyte precursor cells relative to a control.

In the above-mentioned method, the hemocyte precursor cells are preferably hemocyte precursor cells expressing a C5a receptor(s). Increase of the R4 RGS family is preferably an increase of the R4 RGS family mediated by a C5a receptor(s). In the present invention, the R4 RGS family can also be referred to as "R4 RGS family genes" or "R4 RGS family proteins".

The present invention also relates to a method of screening for a substance having an activity to promote maturation into hemocytes, which comprises the steps of:
(a) contacting a test substance with hemocyte precursor cells expressing a C5a receptor(s);
(b) detecting maturation of the hemocyte precursor cells mediated by the C5a receptor(s); and
(c) selecting a test substance that promotes maturation of the hemocyte precursor cells relative to a control.

Furthermore, the present invention relates to a method for detecting the function of a test substance in promoting maturation of hemocyte precursor cells, which comprise the steps of:
(a) contacting a test substance with hemocyte precursor cells;
(b) detecting an increase of R4 RGS family in the hemocyte precursor cells; and
(c) selecting a test substance that promotes the increase of R4 RGS family in the hemocyte precursor cells relative to a control.

Alternatively, the present invention relates to a method for detecting the function of a test substance in promoting maturation of hemocyte precursor cells, which comprise the steps of:
(a) contacting a test substance with hemocyte precursor cells expressing a C5a receptor(s);
(b) detecting maturation of the hemocyte precursor cells mediated by the C5a receptor(s); and
(c) selecting a test substance that promotes maturation of the hemocyte precursor cells relative to a control.

In the present invention, hemocyte is a general term for components in the blood obtained as a result of differentiation of myeloid stem cells. Hemocytes of the present invention are, for example, erythrocytes and platelets, but are not limited thereto.

In the screening methods of the present invention, first, hemocyte precursor cells expressing a C5a receptor(s) are brought into contact with a test substance. The test substance maybe, for example, a single compound such as a naturally-occurring compound, organic compound, inorganic compound, protein, or peptide, as well as a compound library, expression products of a gene library, extracts of cells (for example, hemocyte precursor cells), culture supernatants of cells (for example, hemocyte precursor cells), products of fermentative microorganisms, marine organism extracts, plant extracts, and homogenates of hemocyte precursor cells, but is not limited thereto.

Furthermore, as described later, mixtures of these test substances and RP S19 may also be used as test substances.

In the present invention, "hemocyte precursor cells" refers to cells in the process of maturation from myeloid stem cells into hemocytes. Specifically, examples are erythroblasts in the process of differentiation from myeloid stem cells into erythrocytes, and megakaryocytes in the process of differentiation from myeloid stem cells into platelets, but are not limited thereto.

The most immature erythrocytes are proerythroblasts. In the adult stage, erythropoietin acts on erythroid precursor cells in the bone marrow which differentiate into proerythroblasts. Proerythroblasts mature through the stages of basophilic erythroblast, polychromatic erythroblast, and orthochromatic erythroblast to become reticulocytes, and enter the bloodstream after retention in the bone marrow for one to two days. After another day or two, they become mature erythrocytes. Erythroblasts of the present invention include these proerythroblasts, basophilic erythroblasts, polychromatic erythroblasts, orthochromatic erythroblasts, and reticulocytes.

Furthermore, glycophorin A (CD 235) and transferrin receptor (CD71) are known as cell surface markers that show the degree of erythrocyte differentiation. Alternatively, the following cell surface marker combinations can also be used as cell surface markers that show the degree of erythrocyte differentiation.

Lactoferrin (Lf) and C5a receptor (CD88)
FAS ligand (CD178) and C5a receptor (CD88)

That is, expression of these markers is observed in erythroblasts. Therefore, erythroblasts of the present invention include cells that show expression of these markers.

Megakaryocytes are also cells derived from myeloid stem cells. Pluripotent stem cells (CFU-S) differentiate into megakaryocytes by going through megakaryocyte progenitor cells (CFU-Meg) and megakaryoblasts. Megakaryocytes form protrusions upon maturation, and these separate as fragments to become proplatelets and then platelets. Normally, 4000 to 8000 platelets are formed from a single megakaryocyte. Megakaryocytes of the present invention include megakaryocyte progenitor cells (CFU-Meg) and megakaryoblasts.

In the maturation process from megakaryocytes to platelets, changes in their morphology are observed. The cytoplasmic portion of megakaryocytes deforms to form circular or beaded protrusions called megakaryocyte protrusions, the base of the protrusions eventually constricts, and finally these dissociate as fragments to form small round platelets.

In the present invention, maturation to hemocytes means differentiation of hemocyte precursor cells into hemocytes. For example, in the differentiation of erythroblasts into erythrocytes, the following phenomena are observed:
enucleation of erythroblasts;
increase in the expression of the R4 RGS family genes;
increase in the amount of the R4 RGS family proteins in cells; and
decrease in the expression of the transferrin receptors.

Therefore, when at least one, preferably a few, and more preferably all of these phenomena are observed, one can determine that the erythroblasts have matured into erythrocytes. In the present invention, preferred examples of indicators of erythrocyte differentiation are increase in the expression of the R4 RGS family genes and increase in the amount of the R4 RGS family proteins in cells.

RGS (Regular of G protein signaling) proteins promote endogenous GTP hydrolysis activity of the trimeric G protein α subunit, and are factors that suppress G protein signal transduction. The present inventors showed that among the RGS proteins, those of the R4 RGS family become indicators of differentiation of erythroblasts into erythrocytes. Therefore, according to the present invention, differentiation into erythrocytes can be determined using expression of the R4 RGS family as an indicator. Thus, the present invention relates to methods for selecting erythrocytes, which use expression of the R4 RGS family as an indicator. Expression of the R4 RGS family can be confirmed by methods well known to those skilled in the art. The R4 RGS family includes RGS1, RGS2, RGS3, RGS4, RGS5, RGS8, RGS13, RGS16, RGS18, and RGS21 (Pharmacol. Ther. (2007) 116, 473-495). Hereinbelow, Genbank accession numbers of the nucleotide sequences of these genes and those of the amino acid sequences encoded by the nucleotide sequences are shown.

Nucleotide sequence of human RGS3: NM_017790 (Update Date 12-Mar.-2011)
Amino acid sequence of human RGS3: NP_060260 (Update Date 12-Mar.-2011)
Nucleotide sequence of mouse RGS3: NM_001081650 (Update Date 12-Feb.-2011)
Amino acid sequence of mouse RGS3: NP_001075119 (Update Date 12-Feb.-2011)
Nucleotide sequence of rat RGS3: NM_019340 (Update Date 31-Jan.-2010)
Amino acid sequence of rat RGS3: NP_062213 (Update Date 31-Jan.-2010)
Nucleotide sequence of human RGS1: NM_002922 (Update Date 09-Apr.-2011)
Amino acid sequence of human RGS1: NP_002913 (Update Date 09-Apr.-2011)
Nucleotide sequence of mouse RGS1: NM_015811 (Update Date 13-Mar.-2011)
Amino acid sequence of mouse RGS1: NP_056626 (Update Date 13-Mar.-2011)
Nucleotide sequence of rat RGS1: NM_019336 (Update Date 13-Mar.-2011)
Amino acid sequence of rat RGS1: NP_062209 (Update Date 13-Mar.-2011)
Nucleotide sequence of human RGS2: NM_002923 (Update Date 09-Apr.-2011)
Amino acid sequence of human RGS2: NP_002914 (Update Date 09-Apr.-2011)
Nucleotide sequence of mouse RGS2: NM_009061 (Update Date 10-Apr.-2011)
Amino acid sequence of mouse RGS2: NP_033087 (Update Date 10-Apr.-2011)
Nucleotide sequence of rat RGS2: NM_053453 (Update Date 13-Mar.-2011)
Amino acid sequence of rat RGS2: NP_445905 (Update Date 13-Mar.-2011)
Nucleotide sequence of human RGS4: NM_0001102445 (Update Date 09-Apr.-2011)
Amino acid sequence of human RGS4: NP_001095915 (Update Date 09-Apr.-2011)
Nucleotide sequence of mouse RGS4: NM_009062 (Update Date 13-Mar.-2011)
Amino acid sequence of mouse RGS4: NP_033088 (Update Date 13-Mar.-2011)
Nucleotide sequence of rat RGS4: NM_017214 (Update Date 11-Mar.-2011)
Amino acid sequence of rat RGS4: NP_058910 (Update Date 11-Mar.-2011)
Nucleotide sequence of human RGS5: NM_001195303 (Update Date 12-Mar.-2011)
Amino acid sequence of human RGS5: NP_001182232 (Update Date 12-Mar.-2011)
Nucleotide sequence of mouse RGS5: NM_009063 (Update Date 13-Mar.-2011)
Amino acid sequence of mouse RGS5: NP_033089 (Update Date 13-Mar.-2011)
Nucleotide sequence of rat RGS5: NM_019341 (Update Date 14-Feb.-2010)
Amino acid sequence of rat RGS5: NP_062214 (Update Date 14-Feb.-2010)
Nucleotide sequence of human RGS8: NM_001102450 (Update Date 10-Apr.-2011)
Amino acid sequence of human RGS8: NP_001095920 (Update Date 10-Apr.-2011)
Nucleotide sequence of mouse RGS8: NM_026380 (Update Date 13-Mar.-2011)
Amino acid sequence of mouse RGS8: NP_0080656 (Update Date 13-Mar.-2011)
Nucleotide sequence of rat RGS8: NM_019344 (Update Date 11-Mar.-2011)
Amino acid sequence of rat RGS8: NP_062217 (Update Date 11-Mar.-2011)
Nucleotide sequence of human RGS13: NM_002927 (Update Date 20-Mar.-2011)
Amino acid sequence of human RGS13: NP_002918 (Update Date 20-Mar.-2011)
Nucleotide sequence of mouse RGS13: NM_153171 (Update Date 11-Mar.-2011)
Amino acid sequence of mouse RGS13: NP_694811 (Update Date 11-Mar.-2011)
Nucleotide sequence of rat RGS13: XM_573469 (Update Date 02-Apr.-2010)
Amino acid sequence of rat RGS13: XP_573469 (Update Date 02-Apr.-2010)
Nucleotide sequence of human RGS16: NM_002928 (Update Date 12-Mar.-2011)
Amino acid sequence of human RGS16: NP_002919 (Update Date 12-Mar.-2011)
Nucleotide sequence of mouse RGS16: NM_011267 (Update Date 11-Mar.-2011)
Amino acid sequence of mouse RGS16: NP_035397 (Update Date 11-Mar.-2011)
Nucleotide sequence of rat RGS16: NM_001077589 (Update Date 10-Apr.-2011)
Amino acid sequence of rat RGS16: NP_001071057 (Update Date 10-Apr.-2011)
Nucleotide sequence of human RGS18: NM_130782 (Update Date 10-Apr.-2011)
Amino acid sequence of human RGS18: NP_570138 (Update Date 10-Apr.-2011)
Nucleotide sequence of mouse RGS18: NM_022881 (Update Date 13-Mar.-2011)
Amino acid sequence of mouse RGS18: NP_075019 (Update Date 13-Mar.-2011)
Nucleotide sequence of rat RGS18: NM_0001047084 (Update Date 26-Dec.-2010)
Amino acid sequence of rat RGS18: NP_001040549 (Update Date 26-Dec.-2010)
Nucleotide sequence of human RGS21: NM_001039152 (Update Date 10-Apr.-2011)
Amino acid sequence of human RGS21: NP_001034241 (Update Date 10-Apr.-2011)
Nucleotide sequence of mouse RGS21: XM_889451 (Update Date 19-Oct.-2010)
Amino acid sequence of mouse RGS21: XP_894544 (Update Date 19-Oct.-2010)

For example, in the differentiation of megakaryocytes into platelets, morphological changes such as formation of cell protrusions in megakaryocytes, and formation of small platelets by division from those protrusions are observed. Therefore, megakaryocytes can be judged to have matured (or differentiated) into platelets when such morphological changes are observed.

Furthermore, the term "promotion of maturation" in the present invention means that the degree of differentiation of hemocyte precursor cells into hemocytes progresses. In the present invention, it means "promotion of maturation" as long as there is progress, even a small one, in the degree of differentiation.

In the present invention, any cells can be used as hemocyte precursor cells expressing a C5a receptor(s), as long as a C5a receptor(s) is expressed. Without particular limitations, hemocyte precursor cells expressing a C5a receptor(s) are, for example, hemocyte precursor cells that naturally express a C5a receptor(s), hemocyte precursor cells in which C5a receptor expression is induced by drug treatment, and hemocyte precursor cells in which a C5a receptor(s) is forcibly expressed by genetic engineering. Hemocyte precursor cells are, for example, naturally-occurring hemocyte precursor cells or cell lines derived from hemocyte precursor cells, but are not limited thereto.

In the present invention, hemocyte precursor cells in which C5a receptor expression is induced by drug treatment may be used. Since it is known that C5a receptor(s) is (are) induced in cells subjected to apoptosis stimuli (Nishiura H et al. J Cell Biochem. 2005 94, 540-553), any drug that initiates apoptosis (for example, manganese II) can induce C5a receptor expression.

Without particular limitations, naturally-derived hemocyte precursor cells are, for example, erythroblasts and megakaryocytes isolated from humans, rats, mice, or such, erythroblasts produced by induction of differentiation from bone marrow cells (Wada H et al. Blood (1990) 75: 505-511), and megakaryocytes produced by inducing differentiation of bone marrow cells (Japanese Patent Application Kokai Publication No. (JP-A) H09-313173 (unexamined, published Japanese patent application)). These cells can be obtained by methods known to those skilled in the art. For example, they can be obtained by culturing CD34(+) cells isolated from the bone marrow for a certain period of time in a medium containing IL-3, GM-CSF, SCF, and EPO. In addition, they can also be obtained by methods described in JP-A (Kokai) H09-313173.

Cell lines derived from hemocyte precursor cells include K562 cells (ATCC Number CCL-243), TF-1 cells (ATCC Number CRL-2003), and UT-7 cells (Miura Y et al. Prog. Clin. Biol. Res. 1990 356: 259-270), but are not limited thereto. These cells can be obtained through ATCC or manufacturers of commercially available cells, or by methods described in the above-mentioned documents.

Furthermore, in the present invention, hemocyte precursor cells with forced C5a receptor expression may also be used. Hemocyte precursor cells with forced C5a receptor expression can be obtained by inserting a DNA encoding a C5a receptor into a vector for expressing foreign genes, and then expressing the gene in blood cells.

Expression of the C5a receptor(s) in hemocyte precursor cells can be confirmed by methods such as Western blotting and FACS analysis using anti-C5a antibodies. In FACS analysis, reaction of fluorescence-labeled anti-C5a antibodies with hemocyte precursor cells, followed by measurement of fluorescence from the hemocyte precursor cells enables one to confirm C5a receptor expression in the hemocyte precursor cells. In Western blotting, proteins extracted from hemocyte precursor cells are blotted onto a nitrocellulose membrane or such, and this is subjected to reaction with an anti-C5a antibody, and then coloring reaction is performed using an enzyme-labeled secondary antibody. Expression of the C5a receptor(s) in hemocyte precursor cells can be confirmed by detecting the anti-C5a antibody. C5a-receptor-expressing hemocyte precursor cells of the present invention include cells confirmed by such methods.

The C5a receptor was identified as a receptor of complement C5a which is a leukocyte chemotactic factor. The C5a receptor(s) of the present invention is (are) not limited, so long as they can bind to C5a.

C5a receptor genes and proteins encoded by these genes are known in humans, mice, rats, and such. The Genbank accession numbers of the nucleotide sequences and amino acid sequences of the C5a receptor in the respective animals are shown below. Furthermore, the nucleotide sequence of the human C5a receptor gene is shown in SEQ ID NO: 1, and the amino acid sequence of the protein encoded by this gene is shown in SEQ ID NO: 2. Those skilled in the art can obtain the C5a receptor(s) of humans, mice, or other animals based on known sequence information on C5a receptor(s).

Nucleotide sequence of human C5a receptor: NM_001736 (Update Date 21-Mar.-2010)

Amino acid sequence of human C5a receptor: NP_001727 (Update Date 21-Mar.-2010)

Nucleotide sequence of mouse C5a receptor. NM_001173550 (Update Date 05-Apr.-2010)

Amino acid sequence of mouse C5a receptor: NP_001167021 (Update Date 05-Apr.-2010)

Nucleotide sequence of rat C5a receptor: NM 0001173550 (Update Date 30-Apr.-2010)

Amino acid sequence of rat C5a receptor: NP_001167021 (Update Date 30-Apr.-2010)

In the present invention, C5a receptor(s) is (are) not limited to the above-mentioned examples and include proteins functionally equivalent to the above-mentioned C5a receptor(s). Functionally equivalent proteins bind to RP S19 multimers and cause maturation of hemocyte precursor cells. Such proteins include proteins comprising an amino acid sequence with one or more amino acid substitutions, deletions, additions, and/or insertions in the amino acid sequence of a naturally-occurring C5a receptor. Other methods well known to those skilled in the art for preparing DNAs encoding mutant proteins functionally equivalent to a C5a receptor of the present invention include methods that use hybridization techniques under stringent conditions (Southern E M: J Mol Biol 98: 503, 1975) and polymerase chain reaction (PCR) techniques (Saiki R K, et al: Science 230: 1350, 1985; and Saiki R K, et al: Science 239: 487, 1988).

Those skilled in the art can suitably select stringent hybridization conditions. As an example, pre-hybridization is performed overnight at 42° C. in a hybridization solution containing 25% formamide, or more stringently 50% formamide, 4×SSC, 50 mM Hepes pH 7.0, 10×Denhardt's solution, and 20 µg/mL denatured salmon sperm DNA. Then, a labeled probe is added, and hybridization is performed by incubation overnight at 42° C. A subsequent wash can be performed using a washing solution and temperature conditions of "1×SSC, 0.1% SDS, 37° C." or such. More stringent conditions are "0.5×SSC, 0.1% SDS, 42° C." or such, and even more stringent conditions are "0.2×SSC, 0.1% SDS, 65° C." or such. As hybridization washing conditions become more stringent, isolation of DNA with a high homology to the probe sequence can be expected. However, the above-mentioned combinations of SSC, SDS, and temperature conditions are examples, and those skilled in the art can achieve stringencies similar to those mentioned above by appropriately combining the above-mentioned factors or other determining factors of hybridization stringency (for example, probe concentration, probe length, hybridization reaction time and temperature).

Isolation of DNAs of higher homologies can be expected under conditions of higher stringency such as 6 M urea, 0.4% SDS, and 0.1×SSC. The term "high homology" refers to sequence identities of at least 50% or more, preferably 70% or more, more preferably 90% or more, and most preferably 95% or more over the entire nucleotide sequence. The number of amino acids mutated in a mutant is generally 30 amino acids or less, preferably 15 amino acids or less, and more preferably 5 amino acids or less, even more preferably 3 amino acids or less, and yet even more preferably 2 amino acids or less.

Amino acid sequence identities and nucleotide sequence identities can be determined by using the BLAST algorithm by Karlin and Altschul (Proc. Natl. Acad. Sci. USA 87: 2264-2268, 1990; and Proc. Natl. Acad. Sci. USA 90: 5873, 1993).

Screening methods of the present invention may include a step of contacting cells with a test substance. For example, adding a test substance to a cell culture solution can bring the two into contact.

Furthermore, when the test substance is a protein, for example, introducing a vector containing a DNA encoding the protein into a C5a-receptor-expressing cell can bring the two into contact.

Next, in a screening method of the present invention, maturation of hemocyte precursor cells is detected.

Maturation of hemocyte precursor cells can be carried out, for example, as follows. For example, when the hemocyte precursor cells are erythroblasts, maturation of erythroblasts into erythrocytes can be detected using methods such as:
1) detection of erythroblasts;
2) detection of erythroblast enucleation;
3) detection of increase in the expression of an R4 RGS family gene; and
4) detection of increase in an R4 RGS family protein.

Any one of these maturation indices may be selected as the target of evaluation. Alternatively, multiple indices can serve as the target of evaluation. In the present invention, increase in the expression of an R4 RGS family gene or increase in the amount of an R4 RGS family protein in cells is preferably used as the indicator. Alternatively, steps such as detecting erythrocytes, and/or detecting enucleation of erythroblasts can be included additionally. Specific examples of R4 RGS family are as described above.

The above-mentioned detections of 1) to 4) can be carried out, for example, as follows, but are not limited thereto.

Detection of erythroblasts: By carrying out FACS analyses using a fluorescence-labeled anti-transferrin receptor and an anti-glycophorin A antibody, the group of cells whose cell surface markers are transferrin-receptor (+)/glycophorin A (+) is detected as erythroblasts, and the group of cells whose cell surface markers are transferrin receptor (−)/glycophorin A (+) is detected as erythrocytes.

Alternatively, as substitutes for the anti-transferrin receptor antibody and anti-glycophorin A antibody, the following antibodies may be used.

anti-lactoferrin (Lf) antibody and anti-C5a receptor (CD88) antibody
anti-FAS ligand (CD178) antibody and anti-C5a receptor (CD88) antibody FACS analyses can be carried out by methods known to those skilled in the art.

Detection of erythroblast enucleation: An expression vector containing a gene encoding a fluorescent protein (for example, RFP (red fluorescent protein)) linked to a nuclear localization signal is introduced into hemocyte precursor cells (for example, a K562 cells) to establish in advance hemocyte precursor cells whose nucleus emits red fluorescence. The hemocyte precursor cells are used for screening, and enucleation is detected by observing the red fluorescence.

Detection of increase in R4 RGS family gene expression: RNAs are prepared from hemocyte precursor cells, RT-PCR is performed using primers specific to the R4 RGS family, and increase in the R4 RGS family gene expression is detected by comparison to a control (untreated hemocyte precursor cells) (Nishiura 1H et al. Lab Invest. 2009 June; 89(6): 676-94).

Detection of increase in an R4 RGS family protein: Western blotting, FACS analyses, or such using anti-R4 RGS family antibodies are performed, and increase in an R4 RGS family protein is detected by comparison to a control (untreated hemocyte precursor cells) (Nishiura H et al. Lab Invest. 2009 June; 89(6): 676-94).

The mechanism of promoting apoptosis by RP S19 multimers and C5a receptors is known to include enhancement of RGS family expression. The present inventors discovered that expression of the R4 RGS family is enhanced in the process of hemocyte maturation. Therefore, enhancement of R4 RGS family gene expression and increase of the proteins may serve as indicators for detecting maturation of erythroblasts into hemocytes.

In the present invention, maturation of hemocyte precursor cells (for example, erythroblasts) into hemocytes (for example, erythrocytes) is judged as being promoted when the amount of R4 RGS family gene expression or the amount of an R4 RGS family protein has increased compared to the case when there is no contact with the test substance. Alternatively, maturation of hemocyte precursor cells (for example, erythroblasts) into hemocytes (for example, erythrocytes) is judged as being promoted when results of time-course measurement show that the amount of gene expression or the amount of an R4 RGS family protein in hemocyte precursor cells has increased over time.

Furthermore, in the present invention, when R4 RGS family is expressed, it is determined that maturation of hemocyte precursor cells (for example, erythroblasts) into hemocytes (for example, erythrocytes) has been promoted.

Examples of the R4 RGS family of the present invention preferably include RGS1, RGS2, RGS3, RGS4, RGS5, RGS8, RGS13, RGS16, RGS18, and RGS21, and particularly preferably include RGS1, RGS3, RGS16, and RGS18, but are not limited thereto.

When the hemocyte precursor cells are megakaryocytes, maturation of megakaryocytes into platelets can be determined by detecting platelets. CD41 and von Willebrand factor generally used as surface markers for megakaryocytes, megakaryocyte protrusions, and platelets are commonly expressed among the three, and thus platelets cannot be detected using differentiation markers alone. Detection of platelets requires observation of morphological changes of the cells using a microscope or such. The cell morphology can be clearly observed by specifically staining megakaryocytic cells using an anti-CD41 antibody or an anti-von Willebrand factor antibody (JP-A (Kokai) 2006-94827). When formation of cell protrusions in megakaryocytes and small platelets separated from the protrusions are observed as morphological changes, one can determine that maturation into platelets has been promoted.

As described above, the present inventors discovered that binding of RP S19 multimers to a C5a receptor(s) is involved in the differentiation of hemocyte precursor cells. Therefore, in the screening methods of the present invention, detecting the maturation of hemocyte precursor cells mediated by a C5a receptor(s) is preferred.

One can confirm that maturation of hemocyte precursor cells was caused by mediation of C5a receptor(s), for example, by control experiments such as the ones shown below.

Hemocyte precursor cells that do not express a C5a receptor(s) are prepared as a control. A test substance is brought into contact with the hemocyte precursor cells that do not express a C5a receptor(s). When contacting a certain test substance with hemocyte precursor cells expressing a C5a receptor(s) promotes maturation of the hemocyte precursor cells, whereas contacting the test substance with hemocyte precursor cells that do not express the C5a receptor(s) does not promote maturation of the hemocyte precursor cells, one can determine that this test substance promotes the maturation of hemocyte precursor cells through the C5a receptor(s). Alternatively, when a test substance promotes maturation of hemocyte precursor cells that do not express the C5a receptor(s), this substance may have promoted maturation of hemocyte precursor cells without mediation of the C5a receptor(s).

Thus, the screening methods of the present invention can additionally include the following steps of:
contacting a test substance with hemocyte precursor cells not expressing a C5a receptor(s);
detecting maturation of the hemocyte precursor cells; and
selecting a test substance that does not promote maturation of the hemocyte precursor cells.

The above-mentioned step of "detecting maturation of the hemocyte precursor cells" may also be a step of "detecting an increase of R4 RGS family in the hemocyte precursor cells".

When a substance is brought into contact with hemocyte precursor cells expressing a C5a receptor(s), these additional steps can be carried out after the substance that promotes maturation of hemocyte precursor cells is selected. Alternatively, they can be carried out in parallel with a screening method of the present invention.

Hemocyte precursor cells that do not express a C5a receptor(s) can be prepared by methods known to those skilled in the art. For example, hemocyte precursor cells with suppressed C5a receptor expression can be obtained by suppressing the expression of the C5a receptor-encoding gene using methods such as antisense nucleic acids or siRNA. Alternatively, the C5a receptor function can be inhibited using antibodies against the C5a receptor.

Furthermore, one can confirm that maturation of hemocyte precursor cells is mediated by the C5a receptor(s) based on the binding between the test substance and the C5a receptor(s). For example, when a substance that promotes maturation of hemocyte precursor cells binds to the C5a receptor(s) when brought into contact with hemocyte precursor cells expressing the C5a receptor(s), it can be judged that the substance promotes maturation of hemocyte precursor cells through the C5a receptor(s).

Thus, the screening methods of the present invention can additionally include the following steps of:
contacting a test substance with a C5a receptor(s);
detecting binding of the test substance with the C5a receptor(s); and
selecting a test substance that binds to the C5a receptor(s).

When a substance is brought into contact with hemocyte precursor cells expressing a C5a receptor(s), these additional steps can be carried out after the substance that promotes maturation of the hemocyte precursor cells is selected. Alternatively, through these additional steps, substances that bind to the C5a receptor(s) may be selected in advance. When maturation of hemocyte precursor cells is promoted as a result of contacting a substance selected this way with hemocyte precursor cells expressing the C5a receptor(s), it can be judged that the substance promotes maturation of hemocyte precursor cells through the C5a receptor(s).

Furthermore, one can confirm that maturation of hemocyte precursor cells is mediated through the C5a receptor(s) by using C5a receptor antagonists. For example, when contacted with hemocyte precursor cells expressing the C5a receptor(s), a substance that promotes maturation of hemocyte precursor cells does not promote maturation of hemocyte precursor cells in the presence of a C5a receptor antagonist, it can be judged that the substance promotes maturation of hemocyte precursor cells through the C5a receptor(s).

Thus, the screening methods of the present invention can additionally include the following steps of:
contacting a test substance with hemocyte precursor cells expressing a C5a receptor(s) in the presence of a C5a receptor antagonist;
detecting maturation of the hemocyte precursor cells; and
selecting a test substance that does not promote maturation of the hemocyte precursor cells.

The above-mentioned step of "detecting maturation of the hemocyte precursor cells" may also be a step of "detecting an increase of R4 RGS family in the hemocyte precursor cells".

These additional steps can be carried out after the substance that promotes maturation of hemocyte precursor cells in the absence of a C5a receptor antagonist is selected. Alternatively, they can be carried out in parallel with a screening method of the present invention.

Examples of a C5a receptor antagonist are as follows:
a peptidic antagonist (for example, Ac-Phe-[Orn-Pro-dCha-Trp-Arg] (Finch A M et al. J Med. Chem. 1999 Jun. 3; 42(11):1965-74) and NMePhe-Lys-Pro-dCha-dArg (Konteatis Z D et al. J. Immunol. 1994 Nov. 1; 153(9):4200-5);
a non-peptide antagonist (for example, W-54011 (Sumichika H et al. J Biol. Chem. 2002 Dec. 20; 277(51): 49403-7);
an anti-C5a receptor neutralizing antibody; and
complement C5a.

For methods that use a C5a receptor(s) to screen for test substances that bind to the C5a receptor(s), many methods are known to those skilled in the art. First, a C5a receptor(s) is prepared.

Specifically, a DNA encoding a C5a receptor is inserted into a vector for exogenous gene expression such as pSV2neo, pcDNAI, and pCD8, and the gene is expressed in animal cells and such. Promoters used for expression may be any promoter as long as it can be generally used, and examples include an SV40 early promoter (Rigby In Williamson (ed.), Genetic Engineering Vol. 3. Academic Press, London, p. 83-141 (1982)), EF-1 α promoter (Kim et al. Gene 91, p. 217-223 (1990)), CAG promoter (Niwa et al. Gene 108, p. 193-200 (1991)), RSV LTR promoter (Cullen Methods in Enzymology 152, p. 684-704 (1987), SR α promoter (Takebe et al. Mol. Cell. Biol. 8, p. 466 (1988)), CMV immediate early promoter (Seed and Aruffo Proc. Natl. Acad. Sci. USA 84, p. 3365-3369 (1987)), SV40 late promoter (Gheysen and Fiers J. Mol. Appl. Genet. 1, p. 385-394 (1982)), Adenovirus late promoter (Kaufman et al. Mol. Cell. Biol. 9, p. 946 (1989)), and HSV TK promoter.

To express an exogenous gene by introducing the gene into animal cells, the electroporation method (Chu, G et al. Nucl. Acid Res. 15, 1311-1326 (1987)), calcium phosphate method (Chen, C. and Okayama, H. Mol. Cell. Biol. 7, 2745-2752 (1987)), DEAE dextran method (Lopata, M. A. et al. Nucl. Acids Res. 12, 5707-5717 (1984); Sussman, D. J. and Milman, G. Mol. Cell. Biol. 4, 1642-1643 (1985)), and lipofectin method (Derijard, B. Cell 7, 1025-1037 (1994); Lamb, B. T. et al. Nature Genetics 5, 22-30 (1993); Rabindran, S. K. et al. Science 259, 230-234 (1993)), etc are available, and any of these methods may be used.

The C5a receptor(s) obtained this way can be isolated from inside the host cell or from the host cell membrane, and can be purified as a substantially pure and homogeneous protein. Separation and purification methods used for general protein purification can be used for the separation and purification of proteins, and are not limited in any way. For example, proteins can be separated and purified by appropriately selecting and combining column chromatography, ultrafiltration, salting out, solvent precipitation, solvent extraction, distillation, immunoprecipitation, SDS-polyacrylamide gel electrophoresis, isoelectric focusing, dialysis, recrystallization, and such.

Examples of chromatography are affinity chromatography, ion exchange chromatography, hydrophobic chromatography, gel filtration chromatography, reverse phase chromatography, adsorption chromatography, and such (Strategies for Protein Purification and Characterization: A Laboratory Course Manual. Ed Daniel R. Marshak et al., Cold Spring Harbor Laboratory Press, 1996). These chromatographies can be performed using liquid-phase chromatography such as HPLC and FPLC.

Next, the C5a receptor(s) is brought into contact with a test substance. For example, if the C5a receptor(s) is expressed at the cell surface, the two can be brought into contact with each other by adding the test substance to the culture solution of cells expressing the C5a receptor(s), as mentioned above.

Alternatively, when the C5a receptor(s) is expressed in the cell extract, adding the test substance to the cell extract can bring the two into contact.

Furthermore, if a C5a receptor(s) is in a purified state, adding the test substance to the purified preparation can bring the two into contact.

Binding between a test substance and a C5a receptor(s) can be confirmed by well-known methods for detecting the binding between a receptor and a ligand. For example, the confirmation can be carried out using a label attached to the protein. The type of label includes, for example, fluorescent labels and radiolabels. In addition, measurement methods that use BIACORE, co-immunoprecipitation methods, and such are also known as methods for identifying test substances that bind to the C5a receptor(s).

For example, when detecting binding using a biosensor, one can introduce the C5a receptor(s) prepared by the above-mentioned method into a measuring device. A biosensor that uses the surface plasmon resonance phenomena allows one to observe the interaction between the C5a receptor(s) and the test substance real-time as surface plasmon resonance signals without labeling by the use of a very small amount of polypeptide (for example, BIAcore, manufactured by Pharmacia).

In the present invention, in the screening method or method of detecting the function of promoting maturation of hemocyte precursor cells, test substances that promote the increase of R4 RGS family in hemocyte precursor cells or test substances that promote the maturation of hemocyte precursor cells compared to a control are selected at the end. The selected substances are substances that promote the maturation of hemocyte precursor cells. Such substances may become candidate substances for pharmaceutical agents for treating or preventing hematopoietic failure. Candidate substances identified by a screening method of the present invention can be further tested for their therapeutic effects and safety using anemia model animals, cultured blood cells, or such.

Furthermore, the present inventors discovered that final maturation including enucleation of erythroblasts and pro-platelet formation of megakaryocytes is promoted by the action of RP S19 multimers on the C5a receptors in erythroblasts and megakaryocytes. Therefore, substances that promote RP S19 multimerization may become substances having a promotional activity on maturation into hemocytes. Thus, the present invention relates to methods of screening for substances having a promotional activity on maturation into hemocytes, which comprise the steps below. Alternatively, the present invention relates to methods for detecting the function of a test substance in promoting maturation of hemocyte precursor cells, which comprise the following steps of:

(a) contacting a test substance with hemocyte precursor cells expressing a C5a receptor(s) in the presence of a RP S19 monomer;
(b) detecting an increase of the R4 RGS family in the hemocyte precursor cells; and
(c) selecting a test substance that promotes the increase of R4 RGS family in the hemocyte precursor cells compared to a control.

Furthermore, the present invention relates to methods of screening for substances having an activity of promoting maturation into hemocytes, which comprise the steps below. Alternatively, the present invention relates to methods of detecting the function of a test substance in promoting the maturation of hemocyte precursor cells, which comprise the following steps of:

(a) contacting a test substance with hemocyte precursor cells expressing a C5a receptor(s) in the presence of a RP S19 monomer;
(b) detecting maturation of the hemocyte precursor cells mediated by the C5a receptor(s); and
(c) selecting a test substance that causes maturation of the hemocyte precursor cells compared to when the test substance is absent.

In such screening methods as well, maturation of hemocyte precursor cells is preferably mediated by a C5a receptor(s). Whether or not maturation of hemocyte precursor cells is caused by mediation of a C5a receptor(s) can be confirmed by control experiments such as those mentioned above.

Substances selected by such methods may be substances that promote maturation of hemocyte precursor cells by promoting the multimerization of RP S19. When the substance selected by an above-mentioned screening method or method of detecting a function of promoting maturation of hemocyte precursor cells does not promote hemocyte maturation in the absence of RP S19 and causes RP S19 multimerization, it can be judged that the selected substance is "a substance that promotes maturation of hemocyte precursor cells by promoting RP S19 multimerization". Promotion of hemocyte maturation and binding with RP S19 can be confirmed by the above-mentioned methods. Such substances may also become candidate substances for pharmaceutical agents for treating or preventing hematopoietic failure. Furthermore, they may be used as test substances in a further screening method described later.

Alternatively, the present invention relates to methods of screening for substances having an activity of promoting maturation into hemocytes, which comprise the steps below. Alternatively, the present invention relates to methods for detecting the function of a test substance in promoting maturation of hemocyte precursor cells, which comprise the steps of:
(a) contacting a test substance with a RP S19 monomer;
(b) detecting multimerization of RP S19; and
(c) selecting a test substance that promotes RP S19 multimerization compared to in the absence of the test substance.

Multimerization of RP S19 can be confirmed by performing chromatographies such as gel filtration. Alternatively, it can be confirmed by Western blotting.

In the present invention, when an RP S19 monomer is used, one can detect the function of promoting maturation into hemocytes through RP S19 multimerization. In the screening methods of the present invention, one can detect RP S19 multimerization instead of hemocyte maturation.

The RP S19 gene and the protein encoded by this gene are known in humans, mice, rats, and such. The Genbank accession numbers of the nucleotide sequence and amino acid sequence of RP S19 in the respective animals are shown below. The nucleotide sequence of the human RP S19 gene is shown in SEQ ID NO: 3, and the amino acid sequence of the protein encoded by the gene is shown in SEQ ID NO: 4. Those skilled in the art can obtain RP S19 from humans, mice, and other animals based on known sequence information on RP S19.

Nucleotide sequence of human RP S19 gene: NM_001022 (Update Date 07-May-2010)
Amino acid sequence of human RP S19 protein: NP_0001013 (Update Date 07-May-2010)
Nucleotide sequence of mouse RP S19 gene: NM_023133 (Update Date 01-May-2010)
Amino acid sequence of mouse RP S19 protein: NP_075622 (Update Date 01-May-2010)
Nucleotide sequence of rat RP S19 gene: NM_001037346 (Update Date 01-Feb.-2010)
Amino acid sequence of rat RP 819 protein: NP_001032423 (Update Date 01-Feb.-2010)

RP S19 is not limited to the above examples and proteins functionally equivalent to naturally-occurring RP S19 are included in the present invention. That is, the present invention includes proteins comprising an amino acid sequence with one or more (for example, 2, 3, or 4) amino acid substitutions, deletions, additions, and/or insertions in the amino acid sequence of a naturally-occurring RP S19, and having a function equivalent to that of the naturally-occurring RP S19. Such protein can be obtained by techniques such as PCR and hybridization under stringent conditions as described above. A function of RP S19 is, for example, an activity of becoming multimerized by heparin and activated FXIII, or transglutaminase, and activating maturation of hemocyte precursor cells. Furthermore, it is known that the chimeric protein C5a/RP S19 produced by linking twelve amino acids at the C-terminus of RP S19 to C5a can serve as a substitute for the RP S19 dimer (J. Biochem. (2008) 144, 371-381). A protein functionally equivalent to RP S19 of the present invention includes such protein which can substitute for the function of the RP S19 dimer. C5a/RP S19 can be prepared according to the method described in the above-mentioned document (J. Biochem. (2008) 144, 371-381).

RP S19 used in the screening method of the present invention can be a monomer or multimer. Multimers are, for example, dimers, trimers, tetramers, hexamers, and such, but are not limited thereto. Those skilled in the art can obtain RP S19 in humans, mice, or other animals, or proteins functionally equivalent thereto, based on known RP S19 sequence information as described later. Furthermore, multimers of RP S19 can be obtained by reacting RP S19 monomers with activated FXIII in the presence of heparin (Nishiura H et al. Lab Invest. 1999 79(8): 915-23). Alternatively, RP S19 multimers can be obtained by reacting RP S19 monomers with tissue-type transglutaminase (Nishimura T et al. J. Biochem. 2001 129, 445-454).

In the present invention, a test substance and RP S19 can be mixed in advance and this mixture can be used as the test substance. Thus, the present invention relates to methods of screening for a substance having an activity of promoting maturation into hemocytes, which comprises the steps below. Alternatively, the present invention relates to methods for detecting function of a test substance in promoting maturation of hemocyte precursor cells, which comprises the following steps of:
(a) mixing a test substance with RP S19;
(b) contacting the mixture obtained in step (a) with hemocyte precursor cells expressing a C5a receptor(s);
(c) detecting an increase of the R4 RGS family in the hemocyte precursor cells; and
(d) selecting a test substance that promotes the increase of R4 RGS family in the hemocyte precursor cells compared to a control.

Furthermore, the present invention relates to methods of screening for substances having an activity of promoting maturation into hemocytes, which comprises the steps below. Alternatively, the present invention relates to methods of detecting function of a test substance in promoting maturation of hemocyte precursor cells, which comprises the following steps of:
(a) mixing a test substance with RP S19;
(b) contacting the mixture obtained in step (a) with hemocyte precursor cells expressing a C5a receptor(s);
(c) detecting maturation of the hemocyte precursor cells; and
(d) selecting a test substance that promotes maturation of the hemocyte precursor cells compared to a control.

In the present invention, a substance that binds to a C5a receptor(s) may be a candidate substance having an activity of promoting maturation into hemocytes. Therefore, the present invention relates to methods of screening for a substance having an activity of promoting maturation into hemocytes, which comprise the steps of (a) to (c) below. Alternatively, the present invention relates to methods of detecting function of a test substance in promoting maturation of hemocyte precursor cells, which comprise the following steps of:
(a) contacting a test substance with a C5a receptor(s);
(b) detecting binding between the C5a receptor(s) and the test substance; and
(c) selecting a test substance that binds to the C5a receptor(s).

In such screening methods, the steps of contacting, detecting, and selecting can be carried out using the above-described methods.

Furthermore, the present invention relates to substances having an acquired activity of promoting maturation into hemocytes. Such substances may be candidate substances for therapeutic agents for diseases associated with a decrease in hemocytes such as anemia and thrombocytopenia.

Furthermore, the present invention relates to kits to be used for the screening methods of the present invention. A kit to be used in a method of screening for a substance having an activity of promoting maturation into hemocytes may include elements to be used in the steps of contacting, detecting, and selecting in the above-mentioned screening methods. Examples include hemocyte precursor cells expressing a C5a receptor(s), RP S19, antibodies, and staining solutions. In addition, distilled water, salts, buffers, protein stabilizers, preservatives, and such may be included.

Furthermore, the present invention provides agents for promoting maturation into hemocytes, which contain as an active ingredient either one or both of (i) and (ii) below. A specific embodiment of the promoting agents of the present invention is, for example, an agent for promoting maturation of erythroblasts into erythrocytes, an agent for promoting maturation of megakaryocytes into platelets, and such, but is not limited thereto.
(i) RP S19 multimers
(ii) a substance having an activity of promoting maturation into hemocytes, which is obtained by a screening method of the present invention In addition, the present invention relates to the use of either one or both of the components of the above-mentioned (i) and (ii) in the manufacture of an agent for promoting maturation into hemocytes. Alternatively, the present invention relates to the use of either one or both of the components of the above-mentioned (i) and (ii) in the promotion of maturation into hemocytes. In addition, the present invention relates to methods for manufacturing an agent for promoting maturation into hemocytes, which comprise the step of combining a pharmaceutically acceptable carrier with either one or both of the components of (i) and (ii) described above.

Furthermore, the present invention relates to the use of either one or both of the components of (i) and (ii) described above in the manufacture of a composition for promoting maturation into hemocytes.

"RP S19 multimers" in the promoting agents of the present invention may be naturally-occurring proteins, or can otherwise be prepared as recombinant proteins using known genetic engineering techniques. Furthermore, the organism from which the "RP S19 multimers" in the promoting agents of the present invention are derived is not particularly limited. When they are used for treatment or prevention of human diseases, they are preferably derived from mammals, and most preferably from humans. RP S19 is one of the proteins constituting the ribosome; therefore, it is expressed in all cells that carry out protein synthesis. Therefore, RP S19 can be obtained from any tissue in a living organism. RP S19 can be prepared, for example, by an affinity chromatography method that uses antibodies against RP S19 in a solution of tissue extract taken from a living organism.

On the other hand, recombinant proteins can be prepared, for example, as recombinant polypeptides by methods known to those skilled in the art. Recombinant polypeptides can be prepared, for example, by incorporating a DNA encoding RP S19 into a suitable expression vector, and collecting transformants obtained by introducing this vector into suitable host cells. After an extract is obtained, it is purified by chromatography such as ion exchange, reverse phase, or gel filtration, or by affinity chromatography in which an antibody against RP S19 is immobilized onto the column, or by further combining a plurality of such columns.

When RP S19 is expressed as a fusion polypeptide with a glutathione S-transferase protein or as a recombinant polypeptide with addition of multiple histidines in host cells (for example, an animal cell or *Escherichia coli*), the expressed recombinant polypeptide can be purified using a glutathione column or a nickel column.

With regard to the above-mentioned vectors, for example, when the host is *E. coli*, as long as the vector has an "ori" for amplification in *E. coli*, such that vectors are amplified and prepared in large quantities in *E. coli* (for example, JM109, DH5α, HB101, and XL1Blue) or such, and further has a selection gene for the transformed *E. coli* (for example, a drug resistance gene that allows discrimination using some drug (ampicillin, tetracycline, kanamycin, or chloramphenicol)), the vectors are not particularly limited. The vectors include, for example, M13 vectors, pUC vectors, pBR322, pBluescript, and pCR-Script. In addition to the above vectors, for example, pGEM-T, pDIRECT, and pT7 can also be used for the subcloning and excision of cDNAs. When using vectors to produce RP S19, expression vectors are particularly useful. For expression in, for example, *E. coli*, the expression vector should have the above characteristics to allow amplification of the vector in *E. coli*. In addition, when *E. coli* such as JM109, DH5α, HB101, or XL1-Blue is used as the host, the vector must have a promoter that allows efficient expression in *E. coli*, for example, a lacZ promoter (Ward et al. Nature (1989) 341:544-546; and FASEB J. (1992) 6, 2422-2427), araB promoter (Better et al. Science (1988) 240, 1041-1043), or T7 promoter. Other examples of such vectors include pGEX-5X-1 (manufactured by Pharmacia), "QIAexpress system" (manufactured by QIAGEN), pEGFP, and pET.

Furthermore, the vector may comprise a signal sequence for polypeptide secretion. When producing polypeptides into the periplasm of *E. coli*, the pelB signal sequence (Lei, S. P. et al. J. Bacteriol. (1987) 169, 4379) may be used as signal sequence for polypeptide secretion. For example, calcium chloride methods or electroporation methods may be used to introduce the vector into a host cell.

In addition to *E. coli*, for example, expression vectors derived from mammals (e.g., pcDNA3 (manufactured by Invitrogen), pEGF-BOS (Nucleic Acids Res. 1990, 18(17) p5322), pEF, and pCDM8), insect cells (e.g., "Bac-to-BAC baculovirus expression system" (manufactured by GIBCO-BRL) and pBacPAK8), plants (e.g., pMH1 and pMH2), animal viruses (e.g., pHSV, pMV, and pAdexLcw), retroviruses (e.g., pZIPneo), yeasts (e.g., "Pichia Expression Kit" (manufactured by Invitrogen), pNV11 and SP-Q01), and *Bacillus subtilis* (e.g., pPL608 and pKTH50) may also be used as vectors for producing RP S19.

For expression in animal cells such as CHO, COS, and NIH3T3 cells, the vector must have a promoter necessary for expression in cells, for example, an SV40 promoter (Mulligan et al. Nature (1979) 277, 108), MMLV-LTR promoter, EF1α promoter (Mizushima et al. Nucleic Acids Res. (1990) 18, 5322), or CMV promoter. It is even more preferable that the vector comprises a gene for selecting transformation into cells (for example, a drug-resistance gene that enables discrimination by a drug (such as neomycin and G418)). Examples of vectors with such characteristics include pMAM, pDR2, pBK-RSV, pBK-CMV, pOPRSV, and pOP13.

Furthermore, systems for producing polypeptides in vivo include, for example, those using animals and those using plants. A DNA encoding RP S19 is introduced into an animal or plant to produce RP S19 in the body of the animal or plant, and then the polypeptide is collected.

When animals are used, production systems that use mammals or insects exist. Mammals such as goat, pig, sheep, mouse, and cattle may be used (Vicki Glaser, SPECTRUM Biotechnology Applications 1993). When mammals are used, transgenic animals may be used.

For example, a DNA encoding RP S19 is prepared as a fusion gene with a gene encoding a polypeptide specifically produced in milk, such as goat P-casein. Next, DNA fragments containing this fusion gene are injected into goat embryos, which are then transplanted into female goats. RP S19 can be obtained from milk produced by the transgenic goats born from the goats that received the embryos, or by their offspring. Appropriate hormones may be used on the transgenic goats to increase the quantity of milk containing the polypeptide produced by the transgenic goats (Ebert, K. M. et al., Bio/Technology (1994) 12, 699-702).

Insects such as silkworms may also be used. When silkworms are used, baculoviruses into which a DNA encoding RP S19 has been inserted can be used to infect silkworms, so that RP S19 can be obtained from the body fluids of these silkworms (Susumu, M. et al., Nature (1985) 315, 592-594).

When plants are used, for example, tobacco may be used. When tobacco is used, a DNA encoding RP S19 is inserted into a plant expression vector, for example, pMON 530, and then the vector is introduced into a bacterium such as *Agrobacterium tumefaciens*. The bacteria are then used to infect tobacco such as *Nicotiana tabacum*, and RP S19 can be obtained from the leaves of the tobacco (Julian K.-C. Ma et al., Eur. J. Immunol. (1994) 24, 131-138).

RP S19 thus obtained can be isolated from the inside or outside (such as the medium) of host cells, and purified as a substantially pure and homogeneous polypeptide. Methods used for separating and purifying polypeptides are not limited, and separation and purification methods used in standard polypeptide purification may be applied. Polypeptides can be separated and purified by appropriately selecting or combining, for example, column chromatography, ultrafiltration, salting out, solvent precipitation, solvent extraction, distillation, immunoprecipitation, SDS-polyacrylamide gel electrophoresis, isoelectric focusing, dialysis, recrystallization and such.

RP S19 of the present invention can be modified arbitrarily, or peptides can be deleted partially, by treatment with an appropriate protein modifying enzyme, before or after purification. Such protein modifying enzymes include, for example, trypsins, chymotrypsins, lysyl endopeptidases, protein kinases, and glucosidases.

Once RP S19 is obtained, multimerization of RP S19 can be performed by known methods. For example, as described above, multimerization of RP S19 can be accomplished by reacting RP S19 monomers with activated FXIII in the presence of heparin (Nishiura H et al. Lab Invest. 1999 79(8): 915-23). Alternatively, multimerization of RP S19 can be accomplished by reacting RP S19 monomers with a tissue-type transglutaminase (Nishimura T et al. J. Biochem. 2001 129, 445-454).

Methods for obtaining multimerized RP S19 are also known. For example, RP S19 multimers can be obtained by purification from extracts of synovial lesions of rheumatoid arthritis patients using methods such as reverse phase chromatography (Nishiura H et al. J. Biol. Chem. 1996 271, 878-882), but the methods are not limited thereto.

The RP S19 multimers are, for example, dimers, trimers, tetramers, or hexamers, but are not limited thereto.

In the present invention "RP S19 multimers" can also be referred to as "RP S19 oligomers".

The promoting agents of the present invention can be administered orally or parenterally. Specifically, parenteral administration may be in the form of, for example, injection, transnasally administered agent, transpulmonarily administered agent, or transdermally administered agent. Examples of injections include intravenous injection, intramuscular injection, intraperitoneal injection, and subcutaneous injection that can be administered systemically or locally.

When administering a DNA encoding RP S19 into a living body, viral vectors such as retroviruses, adenoviruses, or Sendai viruses, or non-viral vectors such as liposomes can be used. Examples of administration methods include in vive methods and ex vive methods.

The pharmaceutical agent of the present invention itself may be administered directly to patients, and also it may be administered as a pharmaceutical agent formulated by known formulation methods. For example, it can be used in the form of an injection of a sterile solution or a suspension agent produced by combining with water or other pharmaceutically acceptable solutions. Furthermore, for example, it may be formulated by appropriately combining with a pharmaceutically acceptable carrier or medium, specifically, sterile water, physiological saline, emulsifier, suspending agent, surfactant, stabilizer, vehicle, preservative, or such, and mixed in a unit dose form that meets the generally accepted requirements for preparation of pharmaceuticals. In these preparations, the amount of active ingredient is adjusted such that a suitable amount within a specified range is obtained.

Sterile compositions for injection can be formulated using vehicles such as distilled water for injection, according to standard practice for formulation. Aqueous solutions for injection include, for example, physiological saline and isotonic solutions containing glucose or other adjuvants, for example, D-sorbitol, D-mannose, D-mannitol, and sodium chloride. Appropriate solubilizers, for example, alcohols, specifically ethanol; polyalcohols such as propylene glycol and polyethylene glycol; and non-ionic surfactants such as polysorbate 80™, and HCO-50 may be used in combination.

Oils include sesame and soybean oils. Benzyl benzoate and/or benzyl alcohol can be used as solubilizers in combination. Buffers such as phosphate buffer and sodium acetate buffer; soothing agents such as procaine hydrochloride; stabilizers such as benzyl alcohol and phenol; and/or antioxidants may also be combined. Prepared injections are generally filled into appropriate ampules.

The dose can be appropriately selected in consideration of a patient's age and symptoms. For example, the dosage can be selected from the range of 0.0001 to 1000 mg/kg weight for each administration. Alternatively, the dosage can be selected for example from the range of 0.001 to 100,000 mg/body per patient; however, the dosage of the pharmaceutical agents of the present invention is not limited thereto.

The subject of administration of the pharmaceutical agents of the present invention is mammals. The mammals are preferably humans.

The promoting agents of the present invention may include, instead of an RP S19 multimer, a DNA encoding RP S19 and a substance that promotes multimerization of the translation product of the DNA. The form of the "RP S19-encoding DNA" in the promoting agent of the present invention is not particularly limited, and may be a genomic DNA, cDNA, synthetic DNA, or a vector containing such DNA. The substance that promotes multimerization of a translation product of the RP S19-encoding DNA is, for example, a substance obtained by a screening method of the present invention, but is not limited thereto.

The present invention also relates to methods for producing hemocytes, which comprise the step of bringing hemocyte precursor cells into contact with either one or both of (i) and (ii) below. Specifically, the invention relates to methods for producing erythrocytes, which comprise the step of contacting erythroblasts with either one or both of (i) and (ii) below. Alternatively, the invention relates to methods for producing platelets, which comprise the step of contacting megakaryocytes with either one or both of (i) and (ii) below.

(i) RP S19 multimers (ii) a substance having an activity of promoting maturation into hemocytes, which is obtained by a screening method of the present invention The RP S19 multimers can be obtained by the above-mentioned method. Furthermore, RP S19 multimers of the present invention can also be obtained by preparing from an RP S19-encoding DNA a translation product of the DNA, and then contacting this translation product with a substance that promotes multimerization of the translation product. The RP S19 multimers of the present invention include RP S19 multimers obtained by such method.

The production methods of the present invention can include a step of contacting hemocyte precursor cells with either one or both of (i) and (ii) mentioned above; culturing the hemocyte precursor cells; and collecting erythrocytes and/or platelets from the cells or from their culture supernatant. Thus, the present invention relates to methods for producing hemocytes in vitro. Erythrocytes and/or platelets can be collected and obtained by methods known to those skilled in the art. For example, it can be done by methods described in JP-A (Kokai) 2004-359635 and such.

In the present invention, hemocyte precursor cells derived from patients with diseases associated with a decrease of erythrocytes or platelets, such as patients with hematopoietic failure, can be used as the hemocyte precursor cells. When such patient-derived hemocyte precursor cells are brought into contact with either one or both of (i) and (ii) mentioned above, the cells differentiate into erythrocytes or platelets. By returning the differentiated erythrocytes or platelets into the body of the original patient by methods known to those skilled in the art, the diseases associated with a decrease in erythrocytes and platelets can be improved. Thus, the present invention relates to methods for producing erythrocytes and/or platelets ex vivo.

Alternatively, instead of hemocyte precursor cells derived from patients with diseases associated with a decrease in erythrocytes and platelets, hemocyte precursor cells derived from healthy individuals may be used.

Alternatively, the present invention relates to methods for treating diseases associated with a decrease in erythrocytes and/or platelets, which comprise the step of contacting hemocyte precursor cells with either one or both of (i) and (ii) mentioned above. Diseases associated with decrease in erythrocytes include anemia, but are not limited thereto. Diseases associated with a decrease in platelets include thrombocytopenia, but are not limited thereto.

All prior art references cited herein are incorporated by reference into this specification.

EXAMPLES

Herein below, the present invention will be specifically described with reference to the Examples, but it is not to be construed as being limited thereto.

Example 1

Effects of the RP S19 Multimer/C5a Receptor(s) Mechanism on Hemin-Induced Erythroblastic Differentiation of K562 Cells To confirm involvement of an apoptosis mechanism on erythroid differentiation, apoptosis-resistant substrains were separated from green fluorescent protein (GFP)-expressing K562 cells (GFP-K562 cells). Specifically, 0.5 mM manganese (II) was used on parent cells to induce apoptosis, and cells that remained alive nine days later were collected as apoptosis-resistant cells (MnApoRGFP-K562 cells). Subsequently, 5 mL of control GFP-K562 cells or MnApoRGFP-K562 cells ($5 \times 10^5$ cells/mL) were cultured in a glucose-rich DMEM medium containing 30 nM hemin (iron agent) and 1 nM cyclosporine (immunosuppressing agent), and the processes of erythroblast differentiation were compared. Specifically, while adding 5 mL of the same medium every three days, morphological changes over eight days were observed under a fluorescence microscope FV300 (×3000). As shown in FIG. 1a, in the apoptosis-resistant substrain (MnApoRGFP-K562 cells), a clear delay in the erythroid differentiation process was observed. Next, to investigate the possibility that an apoptosis amplification mechanism mediated by the ribosomal protein S19 multimers (RP S19 oligomers) and the C5a receptor(s) (C5aR) is involved in erythroid differentiation, some of the cells were separated from this culture system every day as samples, and production of the RP S19 multimers and changes in the C5aR expression and transglutaminase type 2 (TGII) expression in both GFP-K562 cells were observed and compared by Western blotting. Specifically, the intracellular proteins were extracted using a loading solution ($10^7$ cells/1 mL loading buffer) having a composition of 9 M urea containing 2% sodium dodecyl sulfate/2% 2-Mercaptoethanol, and 10 µL of each extract was subjected to electrophoresis through a 12% polyacrylamide gel, and this was transferred to an Immobilon-PS$^Q$ membrane. This was pretreated with 1% Block Ace™ for one hour at 22° C., and reacted with a primary antibody (anti-C5aR IgG, anti-RP S19 IgG, or anti-TGII rabbit IgG) for one hour at 22° C. A secondary antibody (horseradish peroxidase (HRP)-conjugated anti-rabbit IgG goat IgG) was reacted for 30 minutes at 22° C., and then the bound HRP was observed using an HCL Plus Western blot detection System™. As shown in FIG. 1b, C5aR gene expression was delayed in the apoptosis-resistant substrain (MnApoRGFP-K562 cells), RP S19 multimer production could not be confirmed even on day 8, and TGII gene expression clearly stayed at a low level. (In this observation, the RP S19 dimer was used to represent multimer (oligomer)).

Example 2

Effects of Manipulating the RP S19 Multimer/C5a Receptor Mechanism on Hemin-Induced Erythroblastic Differentiation of K562 Cells The inventors have already disclosed that in cells made to overexpress the Gln137Asn (Q137N)-RP S19 mutant which cannot form functional cross-linked multimers, promotion of apoptosis by the RP S19 dimer and C5aR is inhibited (Nishiura et al., (2005) S19 ribosomal protein dimer augments metal-induced apoptosis in a mouse fibroblastic cell line by ligation of the C5a receptor. J Cell Biochem 94, 540-553). The inventors have also disclosed that enhancement of expression of the regulator of G protein signaling 3 (RGS3) gene is included in the apoptosis-promoting mechanism by the RP S19 dimer and C5aR (Nishiura et al., (2009) Pro- and anti-apoptotic dual functions of the C5a receptor: involvement of regulator of G protein signaling 3 and extracellular signal-regulated kinase. Lab Invest 89(6):676-94). Accordingly, in order to show that the RP S19 multimer and C5aR are involved in erythroid differentiation, RPS19/GFP-K562 cells, Q137N/GFP-K562 cells, and RGS3/GFP-K562 cells which are GFP-K562 cells made to overexpress wild-type RP S19, Q137N-RP S19, or RGS3, respectively, were prepared, and these were compared to the control GFP-K562 cells (Mock/GFP-K562 cells) in a hemin-induced erythroid differentiation system. FIG. 2a shows results of observing the morphological changes 24 days later under fluorescence microscope FV300 (×3000). Erythroid differentiation was promoted in the RPS19/GFP-K562 cells and RGS3/GFP-K562 cells, and differentiation was clearly delayed in the Q137N/GFP-K562 cells.

To quantitatively see the results of FIG. 2a, FIG. 2b shows the result of observing on an FACS Caliber flow cytometer, the expression and disappearance of glycophorin A and transferrin receptor, which are cell surface markers indicating the degree of erythroid differentiation, after reacting them with antibodies against each of them in PBS containing 5% fetal bovine serum at 4° C. for 30 minutes. Erythroblasts and erythrocytes were represented by transferrin receptor (+)/glycophorin A (+) and transferrin receptor (−)/glycophorin A (+), respectively. Differentiation into erythrocytes in Q137N/GFP-K562 cells was delayed significantly compared to that in RPS19/GFP-K562 cells. On the other hand, in RGS3/GFP-K562 cells, differentiation into erythrocytes took place at a very high rate.

In the case of Mock/GFP-K562 cells, many cells were found to undergo apoptosis by day 24, and apparent erythroid differentiation seemed to be suppressed. In this aspect, there were clearly few cells that underwent apoptosis among Q137N/GFP-K562 cells, and as seen in FIG. 2a, they showed a young and lively morphology.

Example 3

RP S19 Multimers in the Bone Marrow Flush Fluids of Guinea Pig

Figure 3:
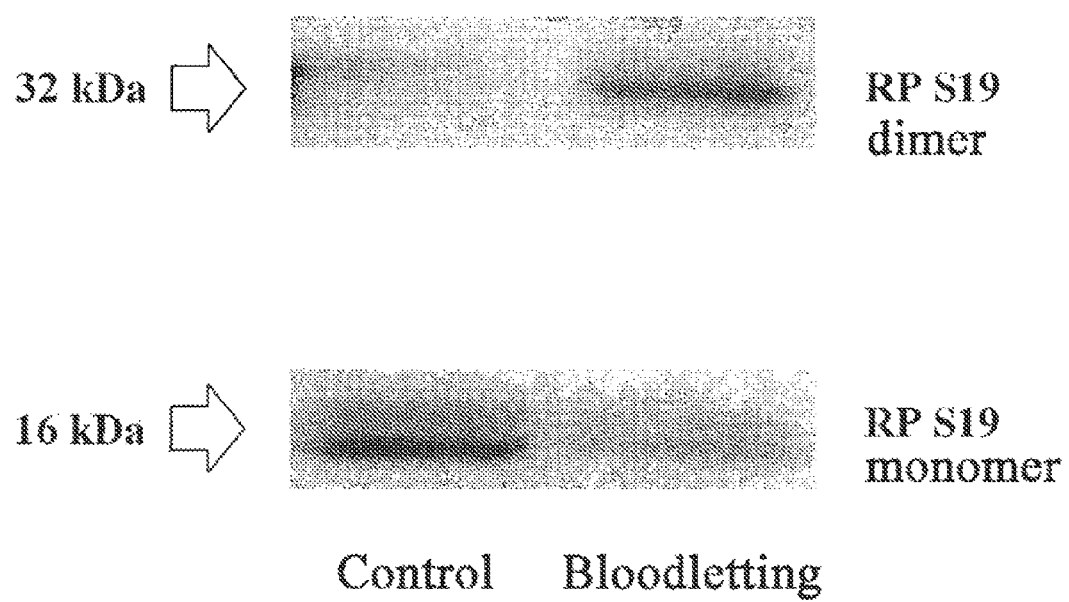
FIG. 3 presents photographs showing presence of the RP S19 multimers in the flush fluid of guinea pig bone marrow. Compared to normal guinea pigs, guinea pigs in a state of hematopoietic stimulation showed promoted RP S19 multimerization in the bone marrow.

If the RP S19 multimers are actually involved in erythroid differentiation, these molecules should be present in the hematopoietic environment of the bone marrow, and the concentration is expected to be increased in the bone marrow where hematopoiesis is enhanced. In order to confirm this in a living organism, normal guinea pigs and guinea pigs in which bloodletting-induced bone marrow hyperplasia was induced by drawing 1 mL of blood from the heart per 200 g of the living organism for three days were prepared. Control femurs were collected from normal guinea pigs, and hyperhematopoietic femurs were collected from the animals three days after bloodletting. The two ends were immediately cut off, 500 μL of PBS was injected three times at one end, and bone marrow flush fluid was obtained from the other end. After the protein concentration was adjusted to 4 mg protein/1 mL PBS, the respective 20-μL samples were subjected to electrophoresis through a 12% polyacrylamide gel, and these were transferred to Immobilon-PS$^Q$ membranes. After reacting them with 1% Block Ace™/anti-RP S19 rabbit IgG/HRP-conjugated anti-rabbit IgG goat IgG, HRP was observed using an ECL kit (since the amino acid sequences of human and guinea pig RP S19 match completely, anti-RP S19 antibodies show reactivity to both RP S19). RP S19 monomers and RP S19 dimers were found in the respective bone marrow flush fluid, and the concentration of the dimers was found to be clearly increased in the hyperplastic bone marrow flush fluid (FIG. 3). Meanwhile, the present inventors have already disclosed that RP S19 monomers are also present in normal blood plasma (Semba et al., (2010) A plasma protein indistinguishable from ribosomal protein S19: Conversion to a monocyte chemotactic factor by a factor XIIIa-catalyzed reaction on activated platelet membrane phosphatidylserine in association with blood coagulation. Am J Pathol 176(3):1542-51). The decrease of monomers in hyperplastic bone marrow flush fluids may be a result that reflects the decrease of space in the sinus due to an increase in hematopoietic tissues.

Example 4

Concentratin of RP S19 Multimers in the Bone Marrow Flush Fluids of Guinea Pigs

Figure 4:
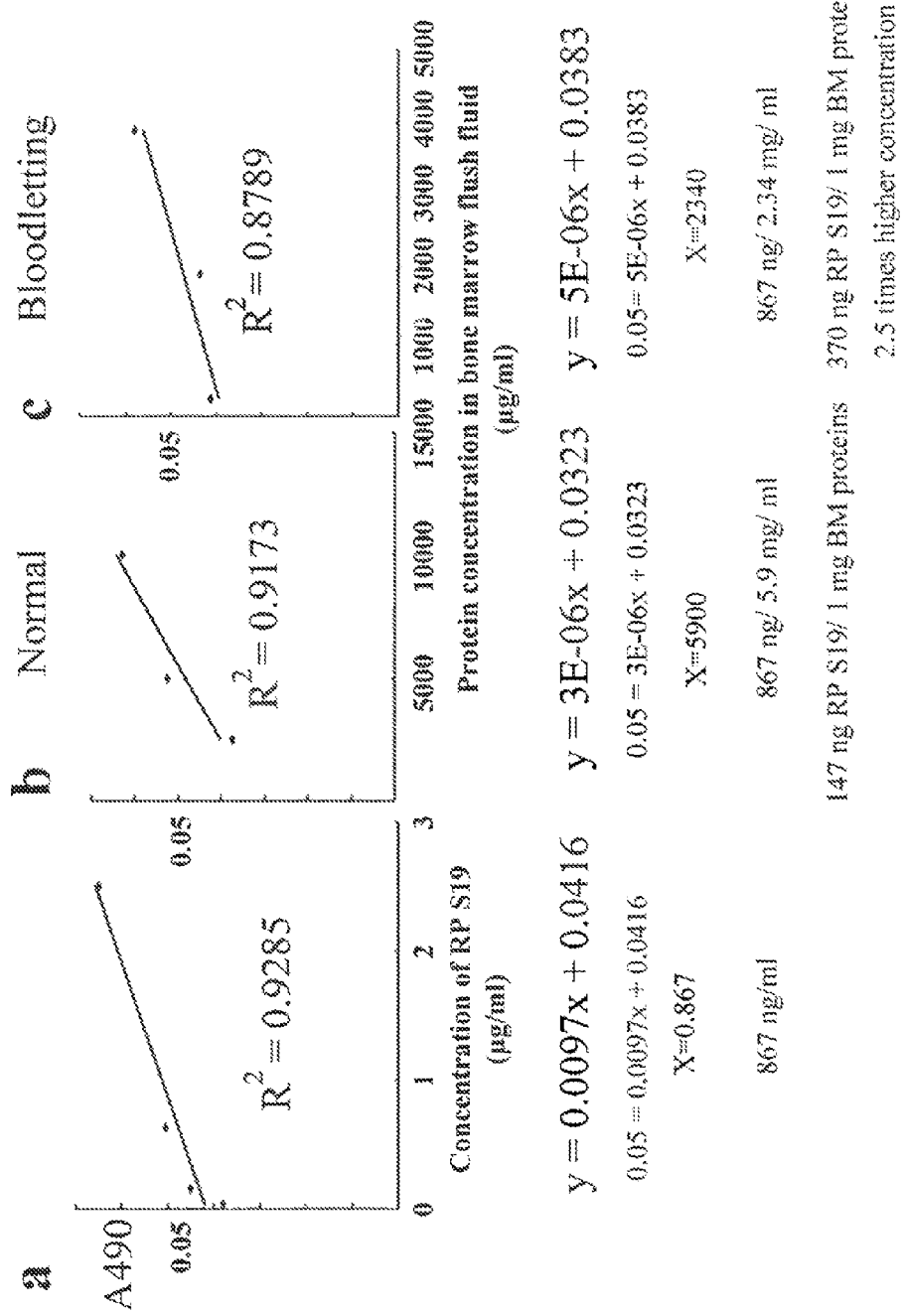
FIG. 4 presents graphs showing concentrations of the RP S19 multimer in the flush fluid of guinea pig bone marrow. Compared to normal guinea pigs, guinea pigs in a state of hematopoietic stimulation had a higher RP S19 concentration in the bone marrow.

Concentration of RP S19 dimers (oligomers) in the bone marrow flush fluid was quantified by sandwich ELISA, and normal bone marrow and bone marrow during hyper-hematopoiesis were compared. Specifically, 50-μL samples of bone marrow flush fluids (4 mg protein/1 mL PBS) diluted with 50% Block Ace™/PBS were added to a 96-well immune plate coated with an anti-RP S19 rabbit IgG, and after reaction, antibody-bound RP S19 dimers were reacted further with a biotinylated anti-RP S19 rabbit IgG and avidin-bound HRP complex. The quantity of HRP was measured as the amount of DAB coloration by absorbance at 490 nm on an ELISA reader. The graph of FIG. 4a is a calibration curve produced using a purified RP S19 recombinant, and the amount of RP S19 oligomer per milligram of bone marrow flush fluid protein was quantified according to the equations shown under the graphs of FIGS. 4b and 4c. Calculation shows that 2.5-times higher concentration of the RP S19 oligomer is present in the bone marrow during hyper-hematopoiesis as compared to that under normal conditions. However, in this method, the monomer and oligomer of RP S19 cannot be differentiated. Considering the monomer to dimer ratio in each of the bone marrow flush fluids according to Western blotting shown in FIG. 3, the concentration of the RP S19 oligomer present in the bone marrow during hyper-hematopoiesis may be several times higher compared to normal.

Purified RP S19 recombinants were produced as follows.

Using the total RNA of hepatic HepG2 cells as template, RP S19 cDNAs were produced by the RT-PCR method, and this was incorporated into a pET11a protein expression vector (pET-RP S19). Using an E. coli protein expression system which uses a BL21(DE3)Lys-S strain transfected with pET-RP S19, recombinant RP S19(rRP S19) was prepared. When the BL21(DE3)Lys-S strain concentration in 500 mL of LB buffer reached 0.5 at A600, 500 mM IPTG was added, and culturing was continued until the BL21 (DE3)Lys-S strain concentration reached 2 at A600.

The BL21(DE3)Lys-S strain was collected by centrifugation, and this was resuspended in 50 mL of 20 mM Tris-HCl pH8.0, 200 mM NaCl. Intracellular proteins were extracted by sonication, and rRP S19 was isolated and purified through an ion exchange (DEAE-sephadex/SP-5PW)/reverse phase (C4) column. Their purities were confirmed by the SDS-PAGE method, and those having a concentration of 1 mg/mL using A280 as the indicator were stored at −70° C. until use.

Example 5

Effects of Neutralizing Bone-Marrow RP S19 Multimer by Anti-C5a Antibody Administration on Erythropoiesis Since RP S19 multimers and C5a bind to the same C5a receptor, cross reactivity can be expected immunologically. FIG. 5a is the result of investigation by Western blotting. Specifically, 24 hours after inducing apoptosis in HL-60 cells introduced with the wild-type RP S19 gene (wild-type RP S19-HL-60) and HL-60 cells introduced with the Gln137Asn mutant RP S19 gene (Q137N-RP S19-HL-60) using 0.5 nM manganese (II), cell extract solutions were produced, and the respective 20-μL samples were subjected to electrophoresis through a 12% polyacrylamide gel, and these were transferred to Immobilon-PS$^Q$ membranes. After pretreatment with 1% Block Ace™, they were reacted with an anti-RP S19 rabbit IgG or anti-human C5a antibody (anti-C5a rabbit IgG), and then after reaction with an HRP-labeled anti-rabbit IgG goat IgG, HRP was visualized using an ECL kit. One can see that the anti-human C5a antibody cross reacts more strongly with the RP S19 multimer. The reason why a very small amount of the RP S19 multimer is produced in Q137N-RP S19-HL-60 is thought to be due to presence of a certain amount of normal RP S19 as an original gene product in HL-60 cells. Meanwhile, the anti-human C5a antibody did not react with C5 in the guinea pig plasma (data not shown). In the experiments shown in FIG. 5b, by comparing the hemoglobin concentration in the blood after collecting blood from the heart immediately before (day 0), one day after (day I), or two days after (day 2) administering 50 μg of an anti-C5a rabbit IgG or control rabbit IgG per 100 g body of the guinea pig to the peritoneal cavity, the effects of bone marrow RP S19 multimer neutralization by the anti-C5a antibody on erythropoiesis were observed. The graph shows the result as a proportion by setting the hemoglobin concentration on day 0 as 100%. The anti-C5a rabbit IgG-administered sample clearly showed stronger anemic conditions. Meanwhile, a slight anemia is seen even with control rabbit IgG administration, because blood loss anemia occurs as collection of 1 mL blood from the heart is necessary each time to measure the blood hemoglobin levels and such.

Example 6

Figure 6:
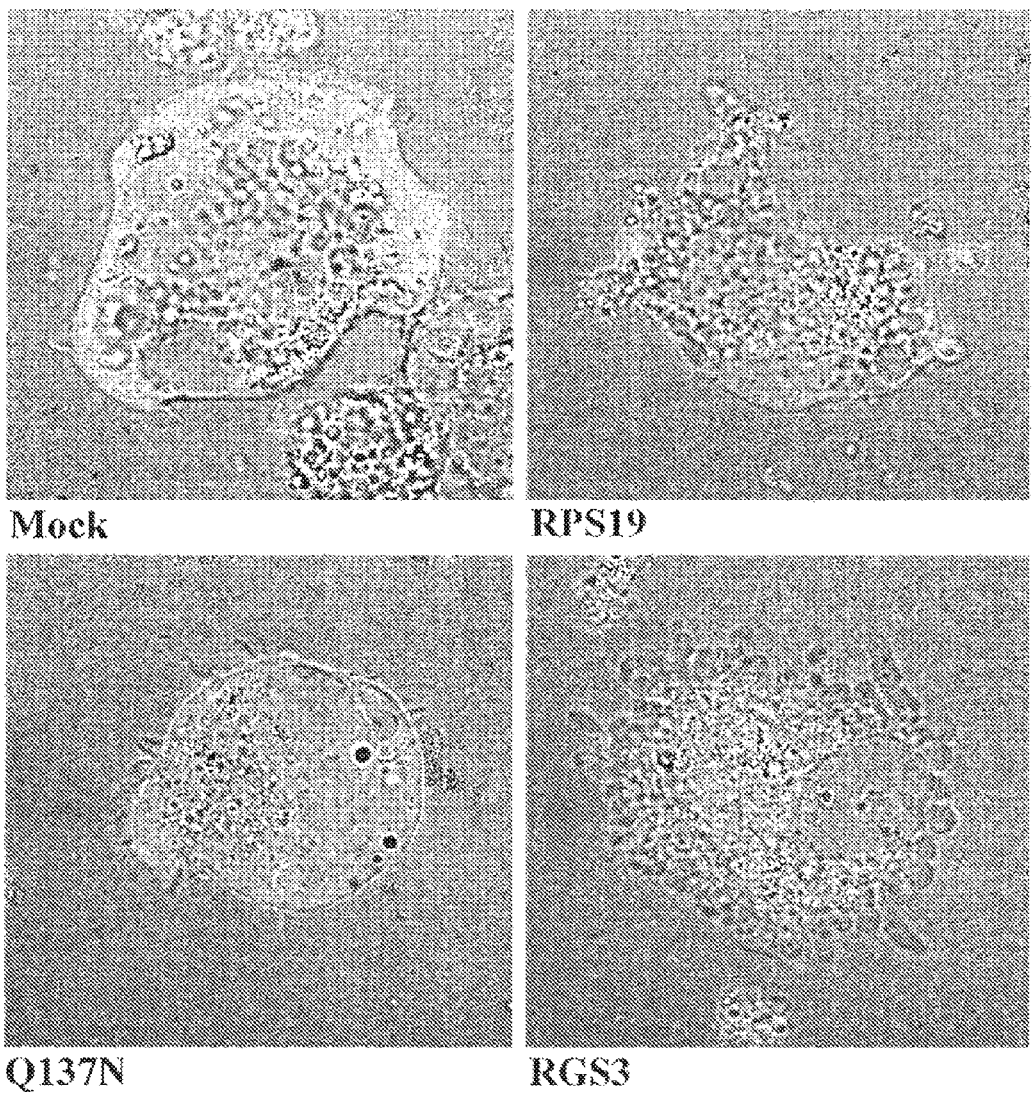
FIG. 6 presents photographs showing effects of manipulating the RP S19 multimer/C5a receptor(s) mechanism on the differentiation of K562 cells into platelet-producing cells by phorbol ester (PMA) induction. In K562 cells with forced expression of RP S19, maturation of platelets is promoted. On the other hand, in K562 cells with forced expression of an RP S19 mutant (Q137N) which cannot form multimers, platelet maturation is not well promoted.

Effects of Manipulating the RP S19 Multimer/C5a Receptor Mechanism on Differentiation of K562 Cells into Platelet-Producing Cells by Phorbol Ester (PMA) Induction When K562 cells are cultured in the presence of phorbol ester instead of hemin, a low percentage is known to differentiate them into platelet-producing cells. Accordingly, culture experiments similar to those indicated in FIG. 2 were carried out in the presence of a phorbol ester. Specifically, 5 mL of Mock/GFP-K562 cells, RPS19/GFP-K562 cells, Q137N/GFP-K562 cells, and RGS3/GFP-K562 cells (5×10$^5$ cells/mL) were cultured in a glucose-rich DMEM medium containing 16 nM phorbol 12-myristate 13-acetate (PMA), 5 mL of the same medium was added every 3 days, and the morphological changes after six days were observed on FV300 (×3000). As in erythroid differentiation, differentiation into platelet producing cells took place at high rates in cells overproducing wild-type RP S19, and at even higher rates in cells overproducing RGS3. On the other hand, this differentiation was suppressed in cells overproducing Gln137Asn-RP S19 (FIG. 6).

Example 7

Figure 5:
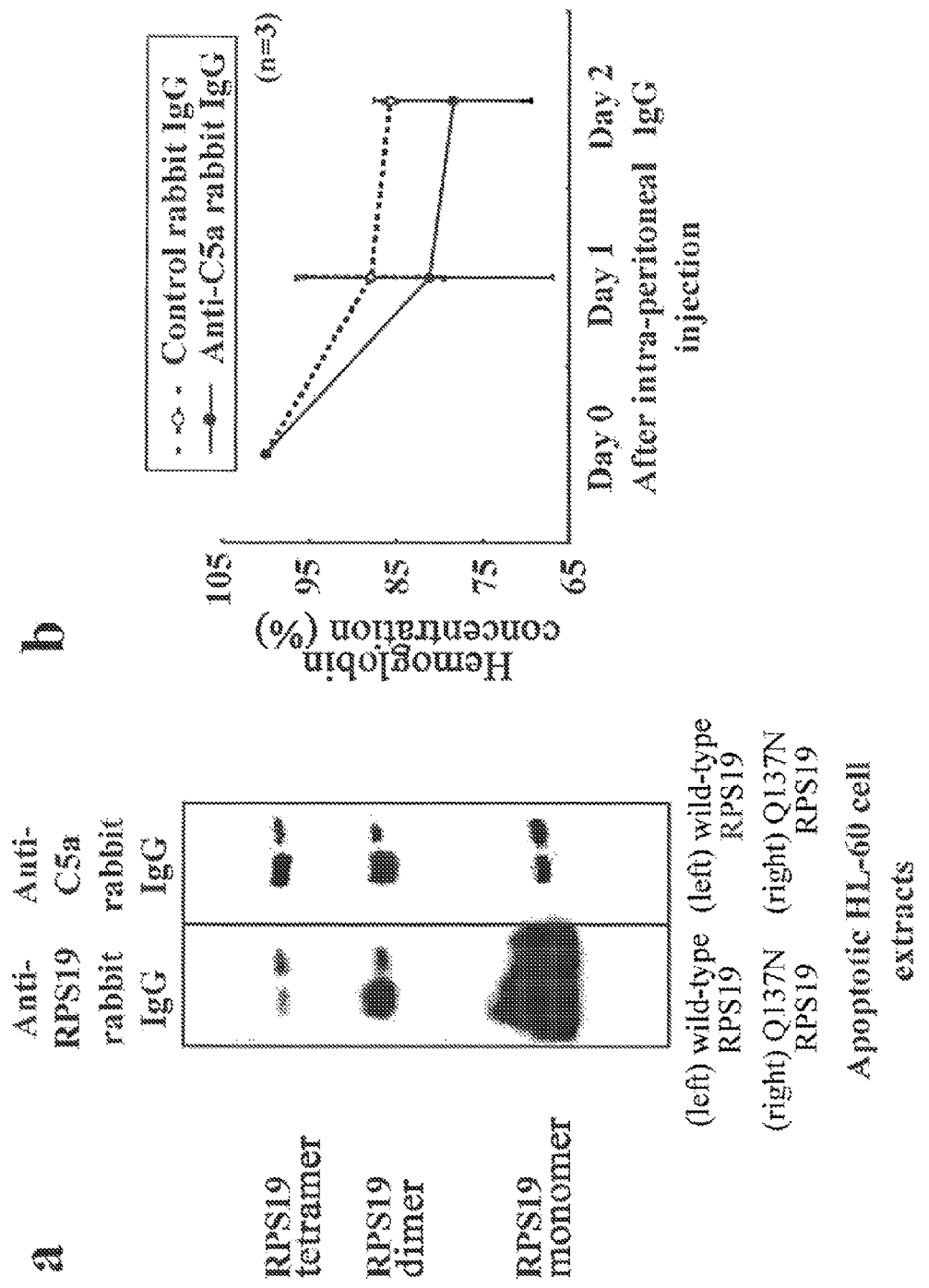
FIG. 5 presents a graph and photographs showing effects on erythropoiesis of neutralizing bone marrow RP S19 multimers by administering an anti-C5a antibody. An anti-C5a rabbit IgG antibody reacts specifically with the RP S19 multimer. As compared to the control group, administration of an anti-C5a rabbit IgG antibody to guinea pigs in a state of hematopoietic stimulation leads to inhibition of erythrocyte recovery.
Figure 7:
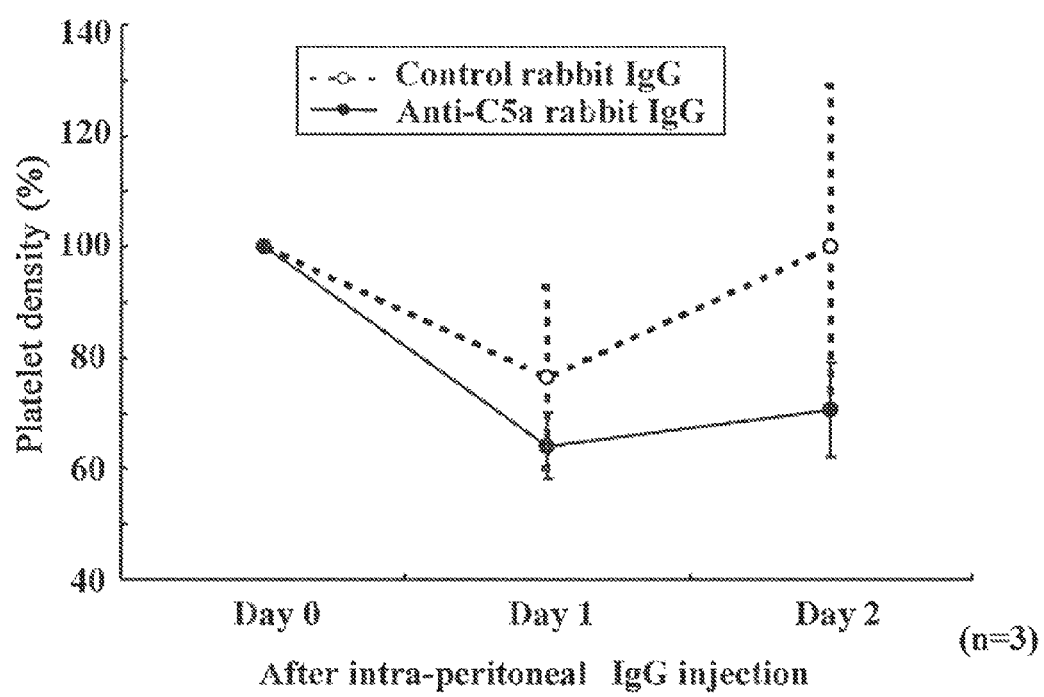
FIG. 7 presents a graph showing effects on thrombopoiesis of neutralizing bone marrow RP S19 multimers by administering an anti-C5a antibody. As compared to the control group, administration of an anti-C5a rabbit IgG antibody to guinea pigs in a state of hematopoietic stimulation leads to inhibition of platelet recovery.

Effects of Neutralizing Bone Marrow RP S19 Multimer by Anti-C5a Antibody Administration on Platelet Hematopoiesis To investigate the actual role of bone marrow RP S19 multimers in platelet hematopoiesis, the exactly same experiment as that shown in FIG. 5 was carried out, and the number of platelets in the cardiac blood collected each day was measured. The results are shown as a percentage with the platelet density immediately before IgG administration (day 0) as 100%. The anti-C5a rabbit IgG-administered group clearly shows more severe thrombocytopenia (FIG. 7). Meanwhile, a slight thrombocytopenia is seen even with control rabbit IgG administration, because blood loss occurs as collecting 1 mL blood from the heart is necessary each time to measure the platelet density and such.

Example 8

The Ability of Manganese Chloride to Assist Induction of K562 Cell Differentiation and Evaluation of Differentiation Markers K562 cells are normally induced to differentiate under conditions of DMEM medium, 10% FBS, 4.5 g glucose, 100 U penicillin/streptomycin, and 30 μM hemin, but for the purpose of assisting induction of differentiation, 0.125 mM manganese chloride was further added (one fourth the concentration for normal apoptosis-inducing ability (0.5 mM)). Cells were collected on days 0, 3, 6, 12, and 15, and the ability to assist induction of erythrocyte differentiation was examined using cell surface markers, glycophorin A (CD235a) and transferrin receptor (CD71), as indicators.

Figures 1, 8:
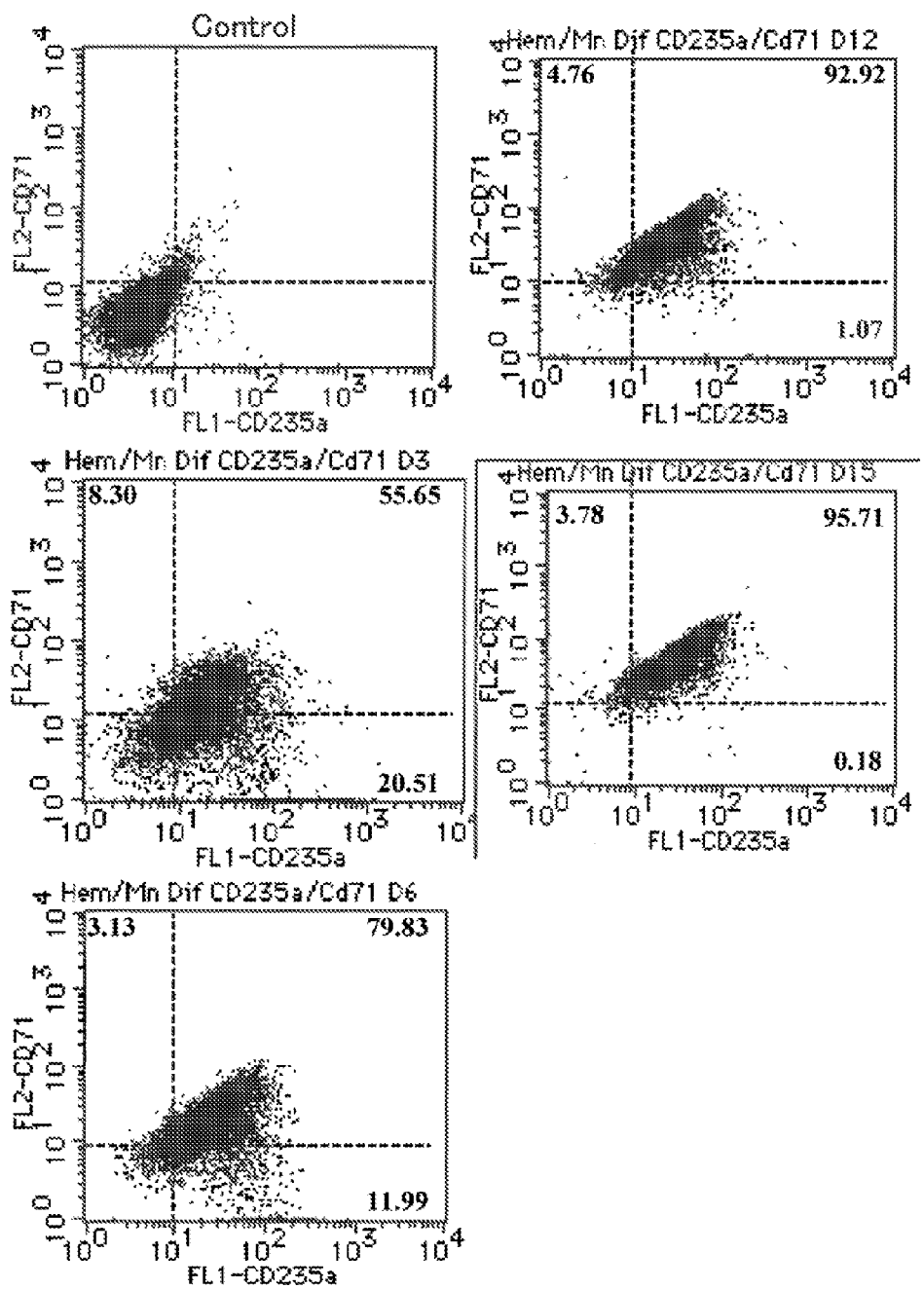
Figures 2, 8:
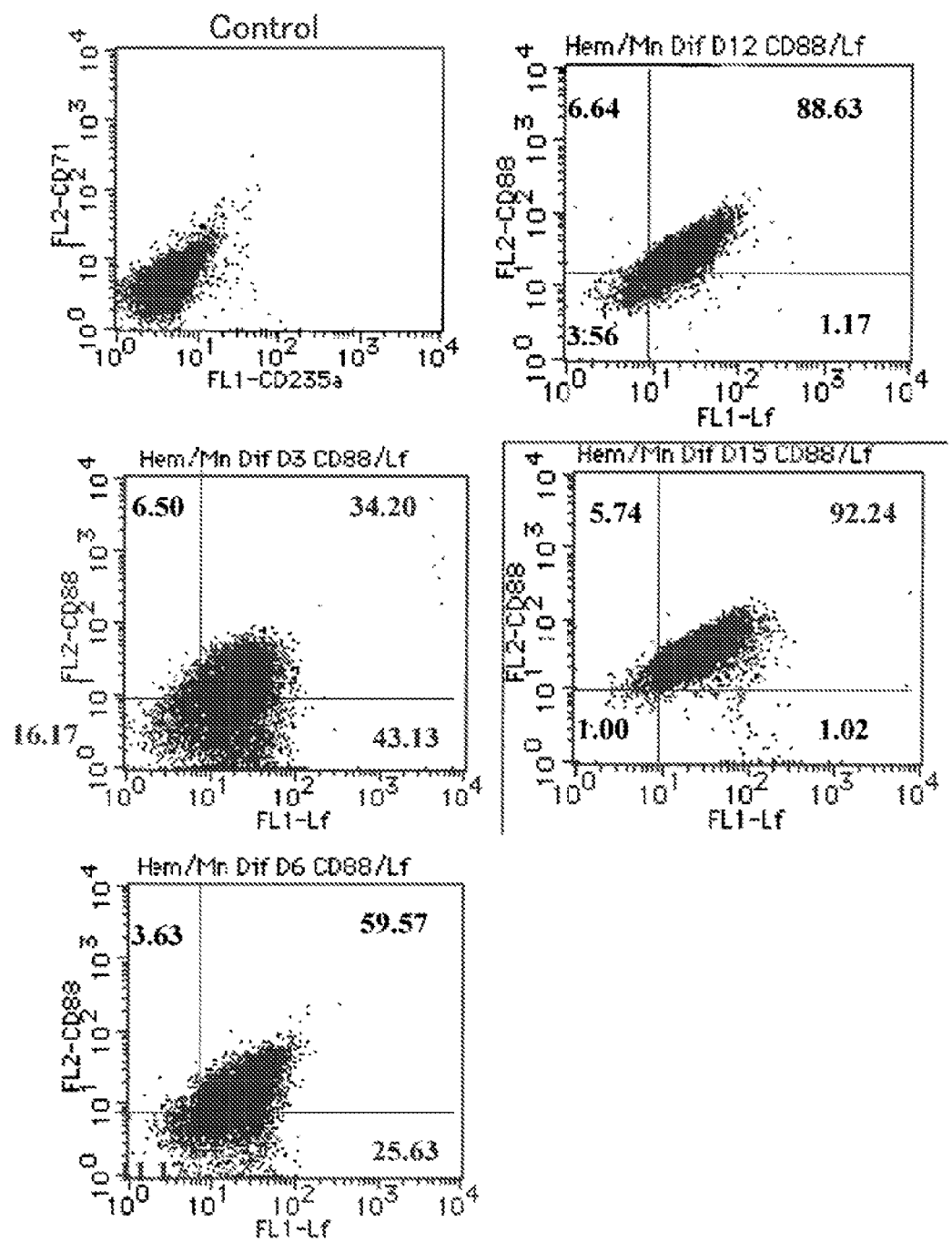
Figures 3, 8:
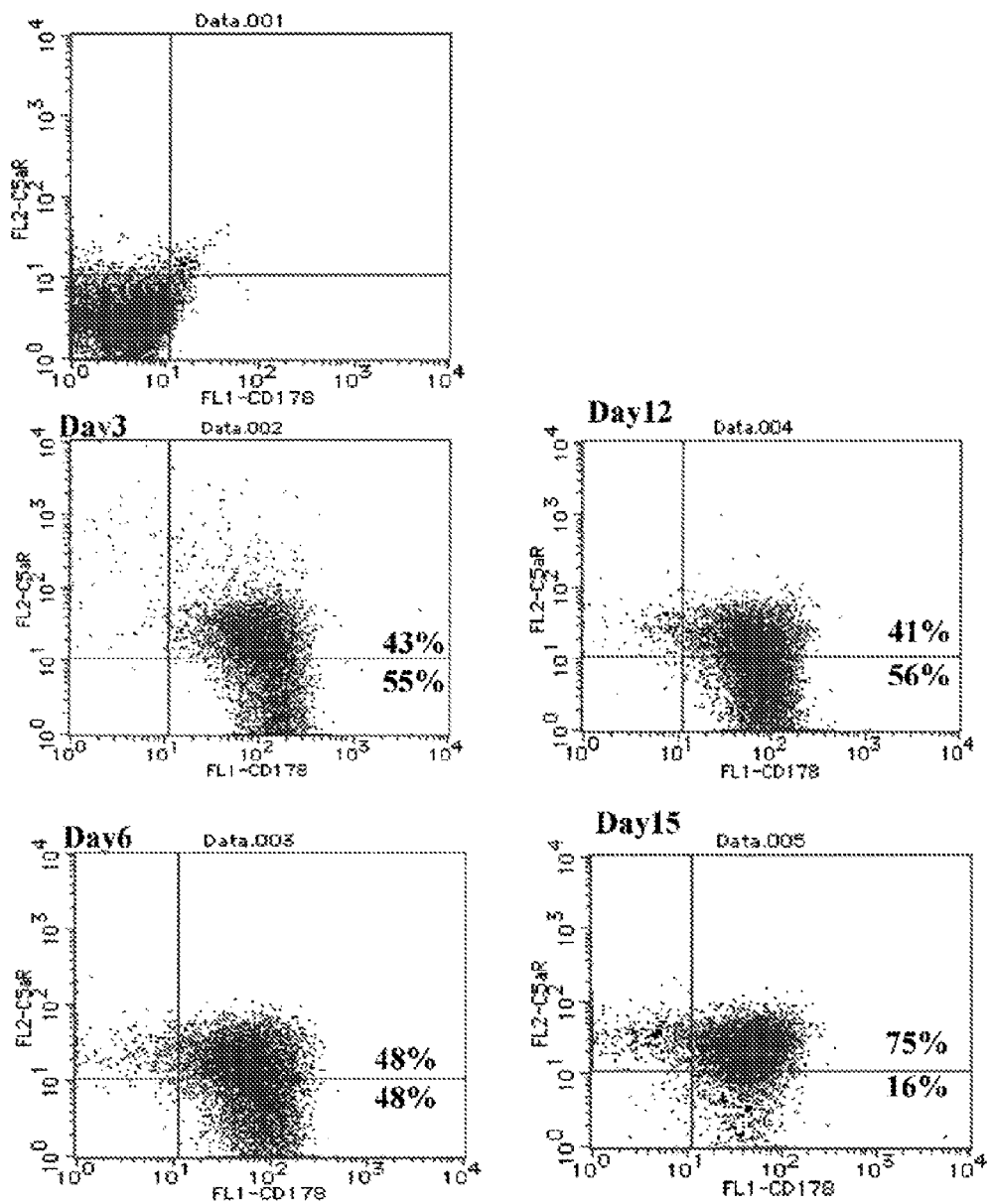

CD235(+/−)/CD71(++) represent K562 proerythroblast-like cells, CD235(+)/CD71(++) represent K562 basophilic erythroblast-like cells, CD235(+)/CD71(+) represent K562 polychromatic erythroblast-like cells, and CD235(+)/CD71 (+/−) represent K562 orthochromatic erythroblast-like cells or reticulocytes. K562 cells are CD71-non-positive cells positioned upstream of pro-erythroblasts. While it takes approximately seven days for the cells to become CD71-positive in manganese-free cultures, cells were confirmed to become CD71-positive on the third day in manganese-supplemented cultures. Therefore, induction of differentiation of K562 cells was assisted by strong apoptotic action of manganese supplementation, and the number of days taken for maturation until erythroblast formation was reduced. Induction of differentiation thereafter was however inhibited (FIG. 8-1).

Using the same system that uses K562 cells for evaluating induction of differentiation, CD235/CD71 which are the existing indicators for induction of erythrocyte differentiation, and the new indicators lactoferrin (Lf)/C5a receptor (CD88) were compared and examined. Cells were collected on days 0, 3, 6, 12, and 15, and the ability to induce differentiation into erythrocytes was examined using Lf/CD88 as the indicators.

Figure 2:
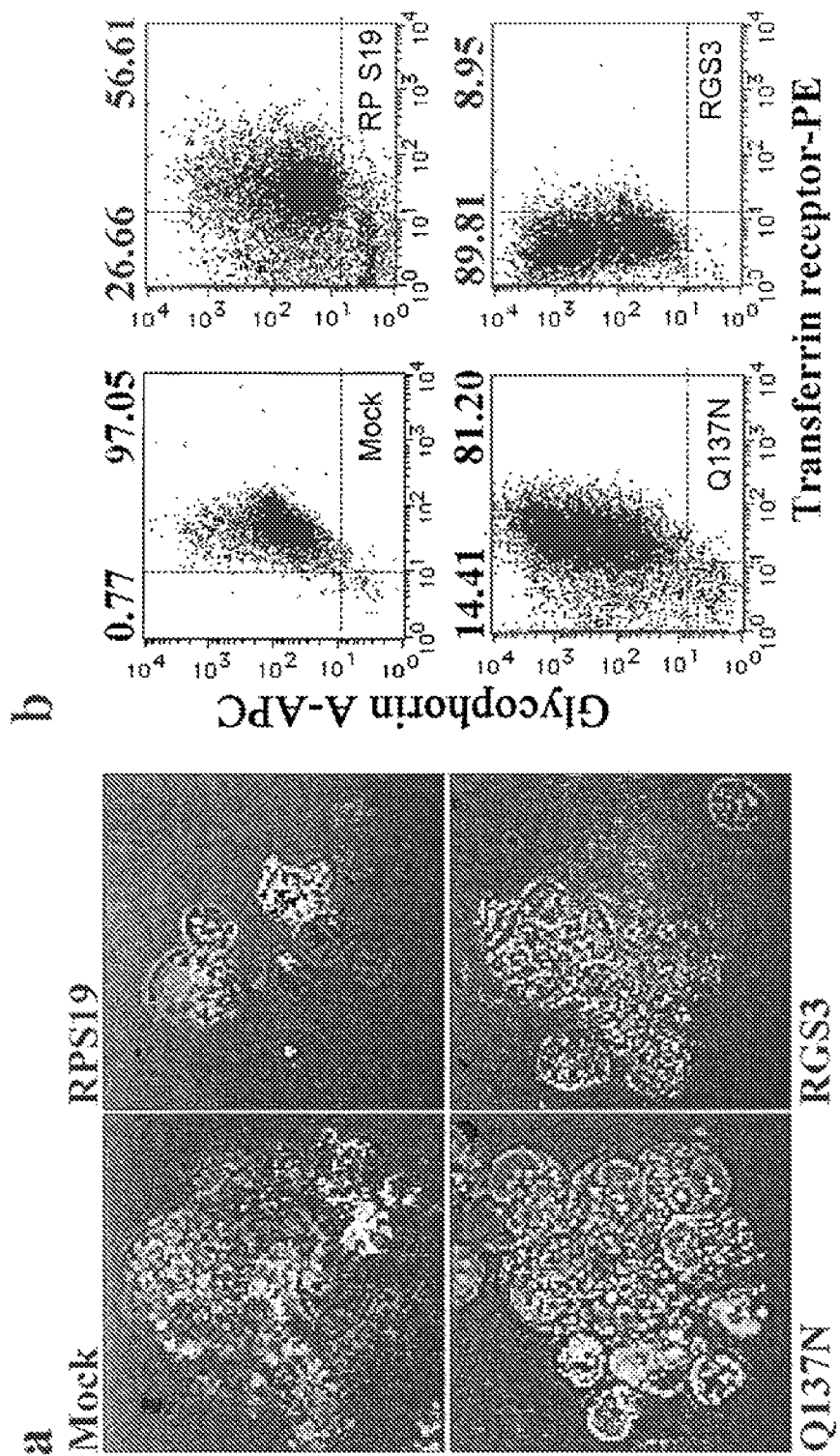
FIG. 2 presents photographs and diagrams showing effects of manipulating the RP S19 multimer/C5a receptor(s) mechanism on hemin-induced erythroblastic differentiation of K562 cells. In K562 cells with forced expression of RP S19, maturation of erythrocytes is promoted. On the other hand, in K562 cells with forced expression of a mutant RP S19 (Q137N) which cannot form multimers, erythrocyte maturation is not well promoted. In K562 cells with forced expression of RGS3, maturation of erythrocytes is remarkably promoted.

Lf(+)/CD88(−) represents K562 proerythroblast-like cells, Lf(+)/CD88(+) represent K562 basophilic erythroblast-like cells, Lf(+/−)/CD88(+) represent K562 polychromatic erythroblast-like cells, and Lf(+/−)/CD88(+/−) represent K562 orthochromatic erythroblast-like cells or reticulocytes. Lf/CD88 were shown to be able to serve as indicators for induction of K562 cell differentiation equivalent to CD235/CD71. Furthermore, induction of the differentiation of K562 cells was assisted by manganese addition, and the number of days taken for maturation until erythroblast formation was reduced. Induction of differentiation thereafter was however inhibited (FIG. 8-2).

Using the same system that uses K562 cells for evaluating induction of differentiation, CD235/CD71 which are the existing indicators for induction of erythrocyte differentiation, and the new indicators FAS ligand (CD178)/C5a receptor (CD88) were compared and examined. Cells were collected on days 0, 3, 6, 12, and 15, and the ability to induce differentiation into erythrocytes was examined using CD178/CD88 as the indicator.

CD178 (+)/CD88(−) represent K562 proerythroblast-like cells, CD178 (+)/CD88(+) represent K562 basophilic erythroblast-like cells, CD178 (+/−)/CD88(+) represent K562 polychromatic erythroblast-like cells, and CD178 (+/−)/CD88(+/−) represent K562 orthochromatic erythroblast-like cells or reticulocytes. CD178/CD88 were shown to be able to serve as indicators for induction of K562 cell differentiation equivalent to CD235/CD71. Furthermore, induction of the differentiation of K562 cells was assisted by adding manganese, and the number of days taken for maturation to form erythroblasts was reduced. Induction of differentiation thereafter was however inhibited (FIG. 8-3).

Example 9

Expression Pattern of RGS3 in Apoptotic Cells

Figure 9:
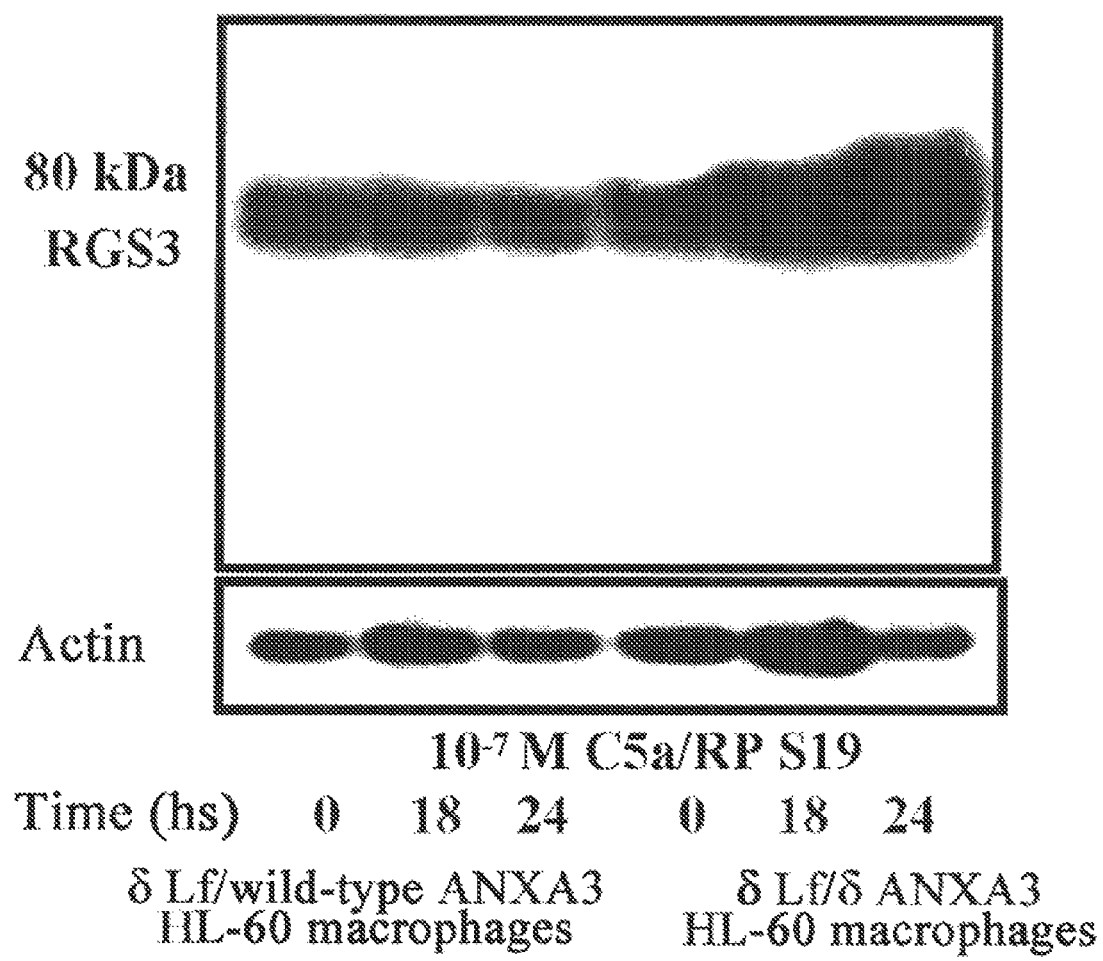
FIG. 9 presents a diagram showing expression of the RGS3 protein in macrophage-like HL-60 cells. After HL-60 cells with forced expression of delta lactoferrin/delta annexin A3 are made to differentiate into macrophage-like cells by addition of phorbol myristate, C5a/RP S19 stimulation leads to an increase in the RGS3 protein expression. This is not observed with wild-type annexin A3.
Figure 10:
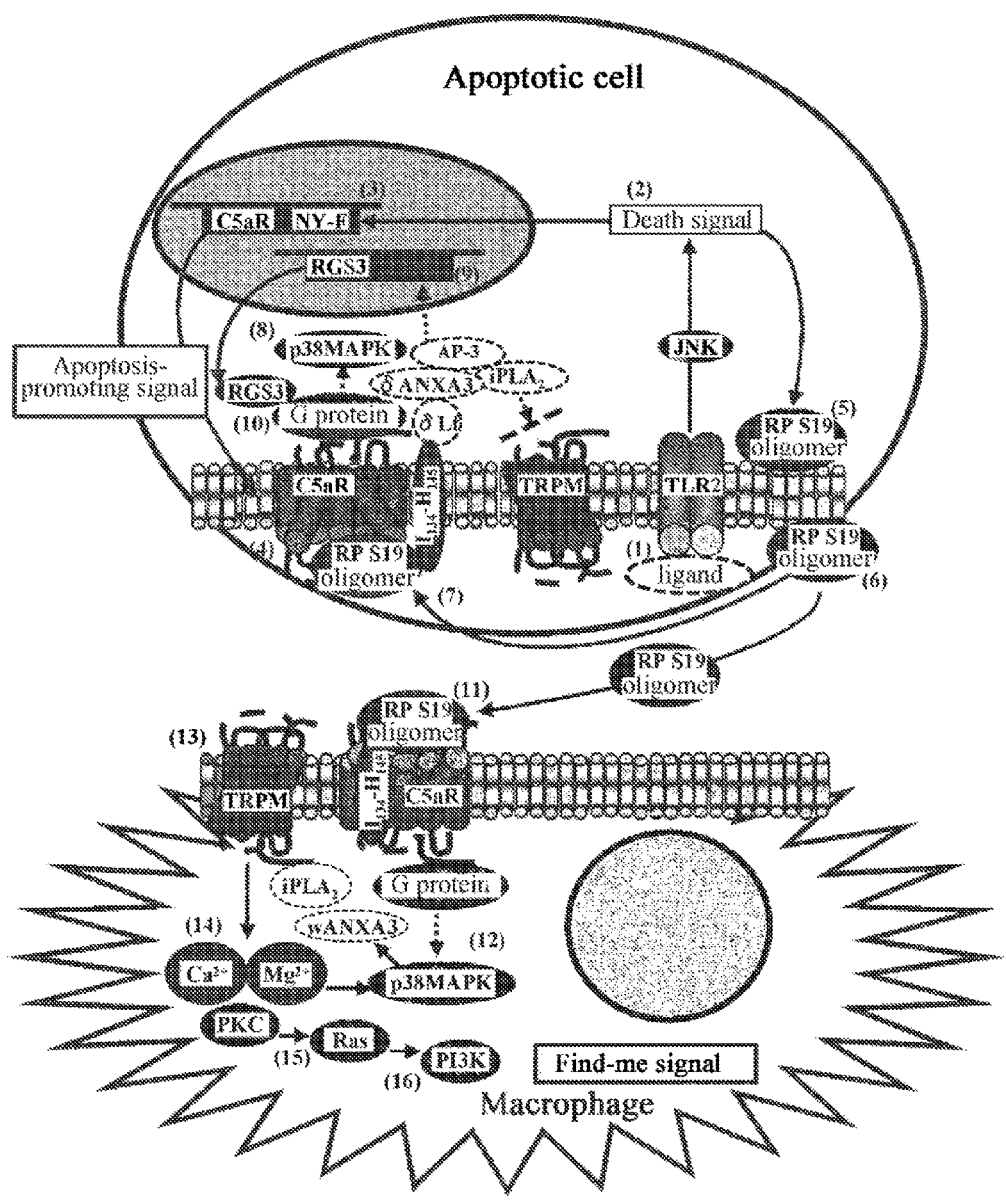
FIG. 10 presents a schematic diagram showing the expression pattern of RGS3 in apoptotic cells. When RP S19 multimers bind to the C5a receptor(s), the C-terminal portion of RP S19 binds to a complex formed between delta lactoferrin and delta annexin A3, and the G-protein-mediated signals of the C5a receptor(s) are inhibited. On the other hand, delta lactoferrin translocates to the nucleus and as a transcription factor, it causes gene expression of RGS3.

Delta lactoferrin/delta annexin A3 or delta lactoferrin/wild-type annexin A3 cDNAs were forcibly expressed in HL-60 cells. The cells were cultured for three days in a DMEM solvent/10% FBS supplemented with 16 nM phorbol myristate, and they were made to differentiate into macrophage-like cells. As a substitute for the RP S19 dimer, C5a/RP S19 ($10^{-7}$ M) was added to macrophage-like HL-60 cells, cells were collected at 0/18/24 hours, and they were made into samples for Western blotting experiments according to standard methods. As a result, RGS3 protein expression increased with time only in HL-60 cells with forced expression of delta lactoferrin/delta annexin A3. Normally, delta lactoferrin/delta annexin A3 are not expressed in macrophages, and thus RGS3 gene expression is not observed. However, when they are forcibly expressed, the cellular properties change to become neutrophil-like and this increased expression of the RGS3 gene (FIG. 9). Delta lactoferrin (δLf) and delta annexin A3 (δANXA3) may be involved as follows in the processes of apoptosis and blood cell maturation: when RP S19 multimers are released from apoptotic cells, they bind to a C5a receptor(s) on the apoptotic cells. The C terminal twelve-amino-acid-residue portion of RP S19 additionally binds to delta lactoferrin. Delta lactoferrin is a transcription factor and it translocates to the nucleus to induce expression of the RGS3 gene and such (FIG. 10).

Example 10

Expression Pattern of the R4 RGS Family in K562 Cell Maturation

Figure 11:
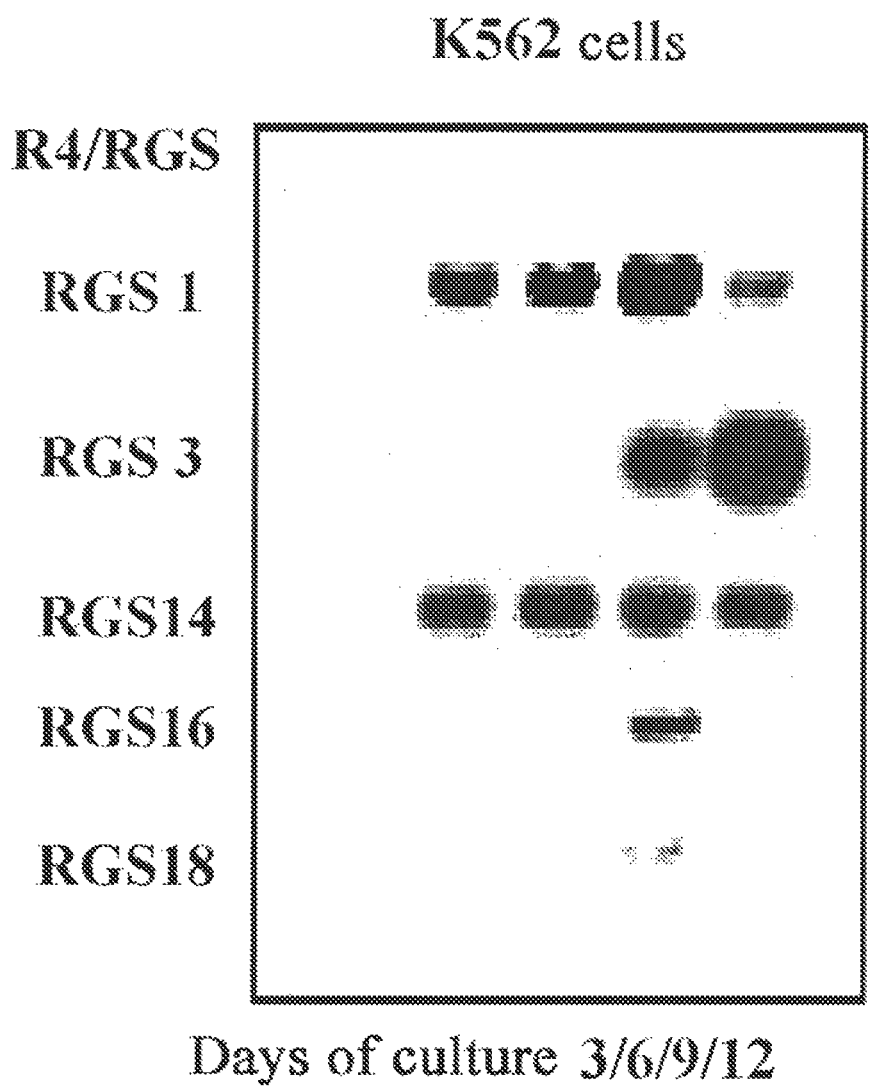
FIG. 11 presents a diagram showing the expression pattern of the R4 RGS family in mature K562 cells. In the maturation process of hemin-stimulated K562 cells, the R4 RGS family (RGS1, RGS3, RGS16, and RGS18) expression increases. On the other hand, RGS14, which is not in the R4 RGS family, does not change.

K562 cells ($5 \times 10^6$ cells/10 mL) were cultured by adding 4.5 g glucose/30 µM hemin to a DMEM solvent, and 2.5 mL of the same solvent was added at 3-day intervals. Cells were collected on days 3, 6, 9, and 12, and were dissolved in 100 µL of SDS Loading Buffer (6 M Urea). 10 µL were run on a 12% SDS-GEL, and after transferring to a blotting membrane, this was reacted with respective antibodies to the R4 RGS family (herein RGS1/RGS3/RGS16/RGS18) and another RGS family (herein, RGS14). The results showed that expression of the R4 RGS family increased, but the expression of RGS14 which belongs to another family did not change (FIG. 11).

INDUSTRIAL APPLICABILITY

Screening methods for substances having an activity of promoting maturation into hemocytes were provided by the present invention. Using such screening methods, substances having an activity of promoting maturation into hemocytes (for example, erythrocytes and platelets) can be obtained. Substances having an activity of promoting maturation into hemocytes are useful as candidate substances for therapeutic agents for diseases associated with a decrease in hemocytes.

In particular, from the present invention, binding of an RP S19 multimer to a C5a receptor(s) was found to be involved in hematopoiesis. Specifically, the actions of RP S19 on the C5a receptor(s) in erythroblasts and megakaryocytes were found to promote the final maturation including enucleation of erythroblasts and proplatelet formation by megakaryocytes. Furthermore, the present invention showed that expression of the R4 RGS family increases with erythrocyte maturation. The findings obtained by the present invention are useful for establishing novel therapeutic methods for diseases associated with a decrease in erythrocytes and platelets such as hematopoietic failure.

The invention claimed is:

1. A method of screening for a substance having an activity of promoting maturation into an erythrocyte in vitro, which comprises:
   (a) contacting a test substance with an erythroblast in vitro;
   (b) detecting an increase in RGS3 in the erythroblast in vitro; and
   (c) selecting a test substance that promotes the increase of RGS3 in the erythroblast compared to a control in vitro.

2. The method of claim 1, wherein the erythroblast expresses a C5a receptor(s) and the increase in RGS3 is promoted via the C5a receptor(s).

3. The method of claim 2, which is performed in the presence of RP S19.

4. The method of claim 2 or 3, which comprises mixing a test substance with an RP S19 monomer prior to (a), and which uses the mixture of the test substance and RP S19 monomer obtained as the test substance in (a).

5. The method of claim 1, wherein (b) further comprises detecting an erythrocyte.

6. The method of claim 1, wherein (b) further comprises detecting enucleation of an erythroblast.

7. The method of claim 1, wherein (b) comprises detecting an increase in the expression of an RGS3 gene.

8. The method of claim 1, wherein (b) comprises detecting an increase in an RGS3 protein.

* * * * *

SEQUENCE LISTING

<160> NUMBER OF SEQ ID NOS: 4

<210> SEQ ID NO 1
<211> LENGTH: 1053
<212> TYPE: DNA
<213> ORGANISM: Homo sapiens

<400> SEQUENCE: 1
atgaactcct tcaattatac caccoctgat tatgggcact atgatgacaa ggataccctg    60

-continued

```
gacctcaaca cccctgtgga taaaacttct aacacgctgc gtgttccaga catcctggcc    120
ttggtcatct ttgcagtcgt cttcctggtg ggagtgctgg gcaatgccct ggtggtctgg    180
gtgacggcat tcgaggccaa gcggaccatc aatgccatct ggttcctcaa cttggcggta    240
gccgacttcc tctcctgcct ggcgctgccc atcttgttca cgtccattgt acagcatcac    300
cactggccct tggcggggc cgcctgcagc atcctgccct ccctcatcct gctcaacatg    360
tacgccagca tcctgctcct ggccaccatc agcgccgacc gctttctgct ggtgtttaaa    420
cccatctggt gccagaactt ccgaggggcc ggcttggcct ggatcgcctg tgccgtggct    480
tggggtttag ccctgctgct gaccataccc tccttcctgt accgggtggt ccgggaggag    540
tactttccac caaggtgtt gtgtggcgtg gactacagcc acgacaaacg gcgggagcga    600
gccgtggcca tcgtccggct ggtcctgggc ttcctgtggc ctctactcac gctcacgatt    660
tgttacactt tcatcctgct ccggacgtgg agccgcaggg ccacgcggtc caccaagaca    720
ctcaaggtgg tggtggcagt ggtggccagt ttctttatct tctggttgcc ctaccaggtg    780
acggggataa tgatgtcctt cctggagcca tcgtcaccca ccttcctgct gctgaataag    840
ctggactccc tgtgtgtctc ctttgcctac atcaactgct gcatcaaccc catcatctac    900
gtggtggccg ccagggctt ccagggccga ctgcggaaat ccctccccag cctcctccgg    960
aacgtgttga ctgaagagtc cgtggttagg gagagcaagt cattcacgcg ctccacagtg   1020
gacactatgg cccagaagac ccaggcagtg tag                                1053
```

<210> SEQ ID NO 2
<211> LENGTH: 350
<212> TYPE: PRT
<213> ORGANISM: Homo sapiens

<400> SEQUENCE: 2

```
Met Asn Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30

Leu Arg Val Pro Asp Ile Leu Ala Leu Val Ile Phe Ala Val Val Phe
        35                  40                  45

Leu Val Gly Val Leu Gly Asn Ala Leu Val Val Trp Val Thr Ala Phe
    50                  55                  60

Glu Ala Lys Arg Thr Ile Asn Ala Ile Trp Phe Leu Asn Leu Ala Val
65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
            100                 105                 110

Pro Ser Leu Ile Leu Leu Asn Met Tyr Ala Ser Ile Leu Leu Leu Ala
        115                 120                 125

Thr Ile Ser Ala Asp Arg Phe Leu Leu Val Phe Lys Pro Ile Trp Cys
    130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
            180                 185                 190
```

| Ser | His | Asp | Lys | Arg | Arg | Glu | Arg | Ala | Val | Ala | Ile | Val | Arg | Leu | Val |
|-----|-----|-----|-----|-----|-----|-----|-----|-----|-----|-----|-----|-----|-----|-----|-----|
|     |     |     | 195 |     |     |     | 200 |     |     |     | 205 |     |     |     |     |

Leu Gly Phe Leu Trp Pro Leu Leu Thr Leu Thr Ile Cys Tyr Thr Phe
            210                 215                 220

Ile Leu Leu Arg Thr Trp Ser Arg Arg Ala Thr Arg Ser Thr Lys Thr
225                 230                 235                 240

Leu Lys Val Val Ala Val Val Ala Ser Phe Ile Phe Trp Leu
                245                 250                 255

Pro Tyr Gln Val Thr Gly Ile Met Met Ser Phe Leu Glu Pro Ser Ser
            260                 265                 270

Pro Thr Phe Leu Leu Leu Asn Lys Leu Asp Ser Leu Cys Val Ser Phe
            275                 280                 285

Ala Tyr Ile Asn Cys Cys Ile Asn Pro Ile Ile Tyr Val Val Ala Gly
            290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Arg Glu Ser Lys Ser Phe Thr
                325                 330                 335

Arg Ser Thr Val Asp Thr Met Ala Gln Lys Thr Gln Ala Val
            340                 345                 350

<210> SEQ ID NO 3
<211> LENGTH: 438
<212> TYPE: DNA
<213> ORGANISM: Homo sapiens

<400> SEQUENCE: 3

```
atgcctggag ttactgtaaa agacgtgaac cagcaggagt tcgtcagagc tctggcagcc     60
ttcctcaaaa agtccgggaa gctgaaagtc cccgaatggg tggataccgt caagctggcc    120
aagcacaaag agcttgctcc ctacgatgag aactggttct acacgcgagc tgcttccaca    180
gcgcggcacc tgtacctccg gggtggcgct ggggttggct ccatgaccaa gatctatggg    240
ggacgtcaga gaaacggcgt catgcccagc cacttcagcc gaggctccaa gagtgtggcc    300
cgccgggtcc tccaagccct ggagggctg aaaatggtgg aaaaggacca agatggcggc    360
cgcaaactga cacctcaggg acaaagagat ctggacagaa tcgccggaca ggtggcagct    420
gccaacaaga agcattag                                                  438
```

<210> SEQ ID NO 4
<211> LENGTH: 145
<212> TYPE: PRT
<213> ORGANISM: Homo sapiens

<400> SEQUENCE: 4

Met Pro Gly Val Thr Val Lys Asp Val Asn Gln Gln Glu Phe Val Arg
1               5                   10                  15

Ala Leu Ala Ala Phe Leu Lys Lys Ser Gly Lys Leu Lys Val Pro Glu
            20                  25                  30

Trp Val Asp Thr Val Lys Leu Ala Lys His Lys Glu Leu Ala Pro Tyr
        35                  40                  45

Asp Glu Asn Trp Phe Tyr Thr Arg Ala Ala Ser Thr Ala Arg His Leu
    50                  55                  60

Tyr Leu Arg Gly Gly Ala Gly Val Gly Ser Met Thr Lys Ile Tyr Gly
65                  70                  75                  80

Gly Arg Gln Arg Asn Gly Val Met Pro Ser His Phe Ser Arg Gly Ser
                85                  90                  95

-continued

```
Lys Ser Val Ala Arg Arg Val Leu Gln Ala Leu Glu Gly Leu Lys Met
        100                 105                 110

Val Glu Lys Asp Gln Asp Gly Gly Arg Lys Leu Thr Pro Gln Gly Gln
        115                 120                 125

Arg Asp Leu Asp Arg Ile Ala Gly Gln Val Ala Ala Ala Asn Lys Lys
        130                 135                 140

His
145
```